(12) United States Patent
Ehnes

(10) Patent No.: US 11,331,179 B2
(45) Date of Patent: May 17, 2022

(54) ENDOVASCULAR SYSTEMS, DEVICES, AND METHODS ALLOWING FOR BRANCH DEVICE PLACEMENT IN CHANNEL OF MAIN GRAFT

(71) Applicant: Endologix LLC, Irvine, CA (US)

(72) Inventor: Dale Ehnes, Forestville, CA (US)

(73) Assignee: Endologix LLC, Irvine, CA (US)

( * ) Notice: Subject to any disclaimer, the term of this patent is extended or adjusted under 35 U.S.C. 154(b) by 7 days.

(21) Appl. No.: 16/607,075

(22) PCT Filed: Apr. 23, 2018

(86) PCT No.: PCT/US2018/028959
§ 371 (c)(1),
(2) Date: Oct. 21, 2019

(87) PCT Pub. No.: WO2018/200420
PCT Pub. Date: Nov. 1, 2018

(65) Prior Publication Data
US 2020/0375722 A1    Dec. 3, 2020

Related U.S. Application Data

(60) Provisional application No. 62/489,213, filed on Apr. 24, 2017.

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01); *A61F 2250/0063* (2013.01)

(58) Field of Classification Search
CPC ................. A61F 2/07; A61F 2002/061; A61F 2002/067; A61F 2250/0063
See application file for complete search history.

(56) References Cited

U.S. PATENT DOCUMENTS

| | | |
|---|---|---|
| 6,645,242 B1 | 11/2003 | Quinn |
| 9,095,456 B2 | 8/2015 | Ivancev et al. |
| 2004/0193254 A1 | 9/2004 | Greenberg et al. |
| 2007/0219621 A1 | 9/2007 | Hartley et al. |
| 2008/0109066 A1 | 5/2008 | Quinn |

(Continued)

FOREIGN PATENT DOCUMENTS

| | | |
|---|---|---|
| JP | 2011-528258 A | 11/2011 |
| WO | WO-2010/008570 A1 | 1/2010 |

OTHER PUBLICATIONS

European Office Action dated Jan. 14, 2021, from application No. 18789929.9.

(Continued)

*Primary Examiner* — Dinah Baria
(74) *Attorney, Agent, or Firm* — Foley & Lardner LLP

(57) ABSTRACT

Endovascular stent grafts in accordance with various embodiments include one or more channels on a main body graft, the one or more channels defining a passageway for receiving one or more branch portions for treating branch vessels. In various embodiments, the one or more channels on the main body graft may be abluminal, adluminal, or weaved, with respect to a stent structure of the main body graft.

15 Claims, 28 Drawing Sheets

(56) References Cited

U.S. PATENT DOCUMENTS

| | | | |
|---|---|---|---|
| 2011/0087318 A1* | 4/2011 | Daugherty | A61F 2/852 623/1.13 |
| 2013/0144373 A1 | 6/2013 | Shahriari | |
| 2013/0268059 A1 | 10/2013 | Hagaman et al. | |
| 2015/0374487 A1 | 12/2015 | Greenberg et al. | |
| 2017/0056215 A1 | 3/2017 | Nagesh et al. | |

OTHER PUBLICATIONS

International Preliminary Report on Patentability dated Nov. 7, 2019, from application No. PCT/US2018/028959.
International Search Report and Written Opinion dated Aug. 31, 2018, from application No. PCT/US2018/028959.
Chinese Office Action dated Jul. 5, 2021, from application No. 201880042355.3.
Japanese Office Action dated Feb. 28, 2022, from application No. 2020-507514, 7 pages.

\* cited by examiner

ENDOVASCULAR SYSTEMS, DEVICES, AND METHODS ALLOWING FOR BRANCH DEVICE PLACEMENT IN CHANNEL OF MAIN GRAFT

CROSS-REFERENCE TO RELATED PATENT APPLICATIONS

This application is a national stage application under 35 U.S.C. § 371 of International Application No. PCT/US2018/028959, filed Apr. 23, 2018, which claims priority to and the benefit of U.S. Provisional Application Ser. No. 62/489,213, filed on Apr. 24, 2017, the entire contents of each of which are incorporated by reference herein in the entireties.

FIELD

One or more embodiments of the present disclosure relate to stent grafts, systems including stent grafts, and methods of using such systems having stent grafts for treating aneurysms.

BACKGROUND

Aneurysms are enlargements or bulges in blood vessels that are often prone to rupture, and therefore, present a serious risk to patients. Aneurysms may occur in any blood vessel but are of particular concern when they occur in the cerebral vasculature or an aorta.

Abdominal aortic aneurysms (AAA's) are classified based on their location within the aorta as well as their shape and complexity. Aneurysms that are located below the renal arteries are referred to as infrarenal abdominal aortic aneurysms. Suprarenal abdominal aortic aneurysms occur above the renal arteries. Thoracic aortic aneurysms (TAA's) occur in the ascending, transverse, or descending part of the upper aorta.

Stent grafts have come into widespread use for the treatment of aneurysms. Various stent grafts provide a graft layer to reestablish a flow lumen through an aneurysm as well as a stent structure to support the graft. In general, an endoluminal repair using a stent graft involves accessing an aneurysm endoluminally through either or both common iliac arteries. The stent graft is then implanted to treat the aneurysm.

SUMMARY OF THE DISCLOSURE

One or more aspects of example embodiments of the present invention are directed to endovascular stent grafts for treating branch vessels. The endovascular stent grafts include one or more channels formed on or within a main body graft, that are configured to receive one or more branch portions therein. In various embodiments, a portion or entirety of the channel may be used or formed to receive the branch portion, and the channel may be abluminal, adluminal, weaved, or any combination within a wall of the main body graft, with respect to a stent structure of the main body graft.

According to an embodiment, a device includes: a main body graft; and a channel formed at least partially on a wall of the main body graft, the channel defining a passageway for receiving a branch portion.

In an embodiment, the device may further include a stent configured to support the main body graft.

In an embodiment, the channel may be abluminal with respect to the stent.

In an embodiment, the channel may be adluminal with respect to the stent.

In an embodiment, a first portion of the channel may be abluminal with respect to the stent and a second portion of the channel may be adluminal with respect to the stent.

In an embodiment, the channel may be disposed between layers forming the main body graft.

In an embodiment, the channel may be located on a first side of the main body graft, and a second side of the main body graft opposite the first side may include a plurality of pleated portions.

In an embodiment, the first side may not be pleated.

According to an embodiment, a system includes: a branch portion including a stent graft; a main body graft; and a channel formed at least partially within a wall of the main body graft, the channel defining a passageway for receiving the branch portion.

In an embodiment, the system may further include a stent configured to support the main body graft.

In an embodiment, the channel may be abluminal with respect to the stent.

In an embodiment, the channel may be adluminal with respect to the stent.

In an embodiment, a first portion of the channel may be abluminal with respect to the stent and a second portion of the channel may be adluminal with respect to the stent.

In an embodiment, the channel may be disposed between layers forming the main body graft.

In an embodiment, the channel may be located on a first side of the main body graft, and a second side of the main body graft opposite the first side may include a plurality of pleated portions.

In an embodiment, the first side may not be pleated.

According to an embodiment, a method includes: forming a main body stent graft; and forming a channel at least partially on a wall of the main body graft, the channel defining a passageway for receiving a branch portion.

In an embodiment, the forming of the main body stent graft may include: forming one or more inner graft layers; and disposing a stent structure on the one or more inner graft layers.

In an embodiment, the forming of the channel may include: disposing an insulator sheet on the stent structure; forming one or more outer graft layers on the insulator sheet and the stent structure; heating the main body stent graft; and removing the insulator sheet.

In an embodiment, the insulator sheet may include polyoxydiphenylene pyromellitimide.

In an embodiment, the insulator sheet may be wrapped with a graft material, and the graft material may fuse with at least one of the inner graft layers or outer graft layers when the main body stent graft is heated.

In an embodiment, the method may further include: disposing a first separator sheet between the insulator sheet and the stent structure; and disposing a second separator sheet between the insulator sheet and the stent structure, the second separator sheet being spaced apart from the first separator sheet to define a space therebetween. The graft material may fuse with at least one of the inner graft layers or outer graft layers in the space when the main body stent graft is heated.

DETAILED DESCRIPTION

Figure 1:
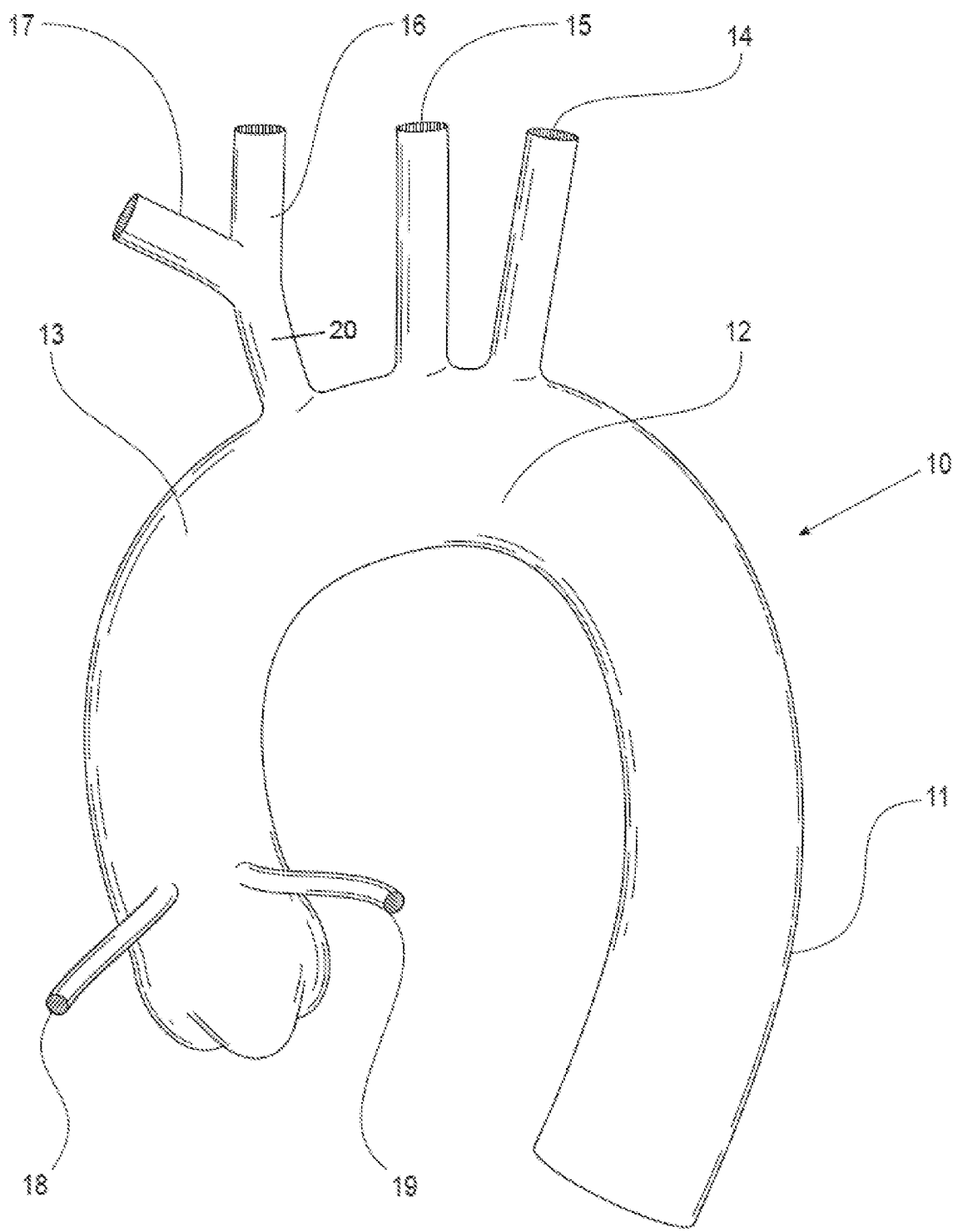
FIG. 1 shows an aorta including an aortic arch.

Hereinafter, example embodiments will be described in more detail with reference to the accompanying drawings. The present disclosure, however, may be embodied in various different forms, and should not be construed as being limited to the illustrated embodiments herein. Rather, these embodiments are provided as examples so that this disclosure will be thorough and complete, and will fully convey the aspects and features of the present disclosure to those skilled in the art. Unless otherwise noted, like reference numerals denote like elements throughout the attached drawings and the written description, and thus, descriptions thereof may not be repeated.

It will be understood that the aspects and features of the present disclosure, as generally described herein, and illustrated in the figures, may be arranged, substituted, combined, and designed in a wide variety of different configurations, all of which are explicitly contemplated and are a part of this disclosure. Accordingly, descriptions of features or aspects within each example embodiment should typically be considered as available for other similar features or aspects in other example embodiments.

One or more embodiments relate to improvements when compared to sandwiched branch devices, and address challenges with regard to sandwiched, parallel, and/or double barrel branch endografting. One or more embodiments relate to addressing gutter sealing or main body endograft oversizing considerations. One or more embodiments of endovascular devices disclosed herein provide devices and methods of deployment where one or more branch receiving channels are formed on or within the wall of a main body stent graft.

Various embodiments of a stent graft device with a channel in a main body stent graft for receiving a branch portion may be used in any vascular system, such as peripheral, hypogastric, visceral vessels, or thoracic. In some embodiments the stent graft device may be used as an accessory system to a previously deployed descending thoracic system, and may be utilized to successively build up into the thoracic arch as needed or desired.

FIG. 1 is a typical configuration of an aorta 10 of a human. The aorta 10 includes a descending aorta portion 11 (e.g., a distal aortic portion), an aortic arch portion 12, and an ascending aorta portion 13 (e.g., a proximal aortic portion). The aorta 10 is fluidically connected to the left subclavian artery 14, the left common carotid artery 15, the right common carotid artery 16, the right subclavian artery 17, the right coronary artery 18, and the left coronary artery 19. The great vessels extend from the aortic arch 12, and include the innominate artery (also known as the brachiocephalic artery) 20, the left common carotid artery 15, and the left subclavian artery 14, which are collectively referred to as the aortic arch vessels. The innominate artery (also known as the brachiocephalic artery) 20 divides into the right common carotid artery 16 and the right subclavian artery 17.

Figure 2A:
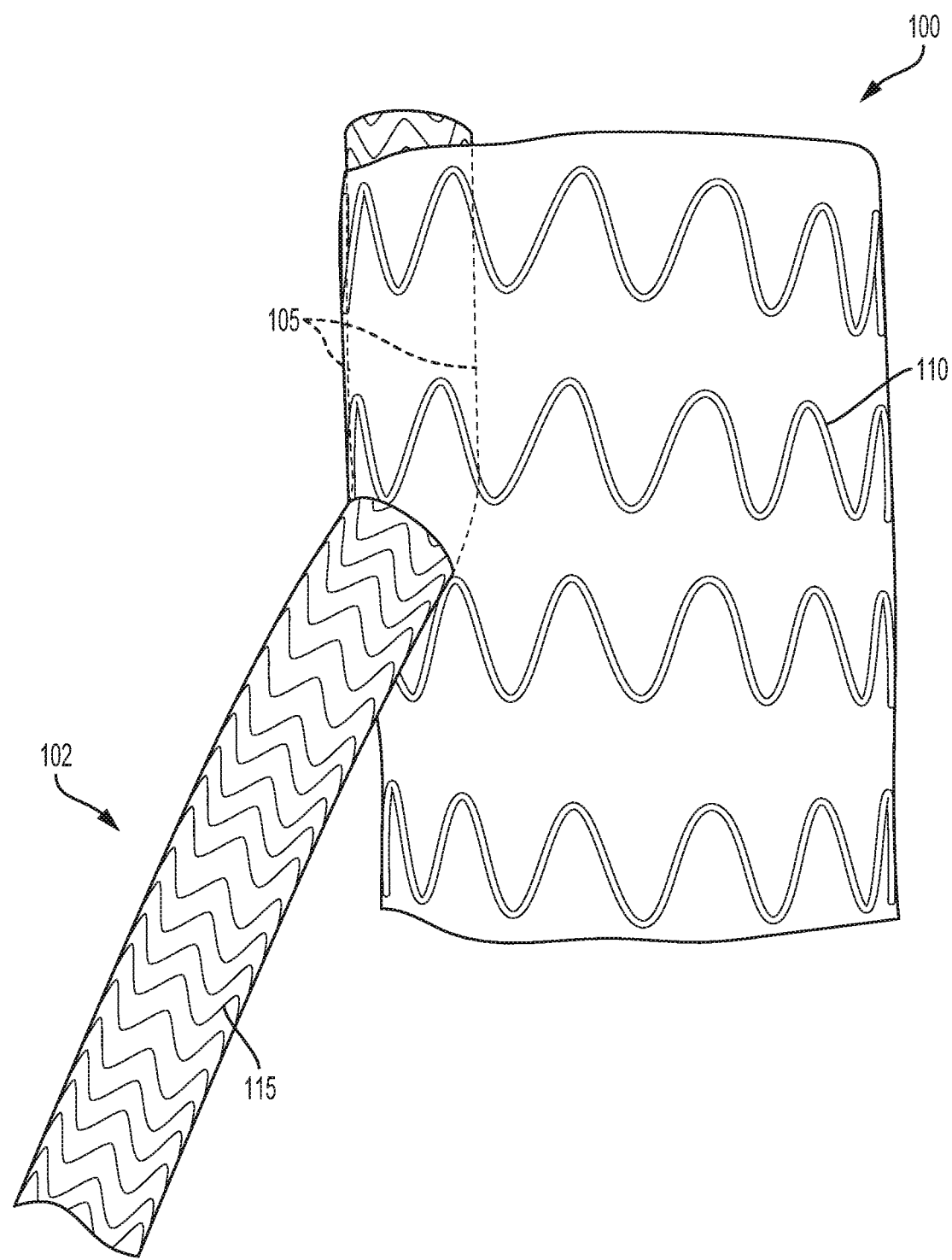
FIG. 2A shows an endovascular system in accordance with an embodiment.
Figure 2B:
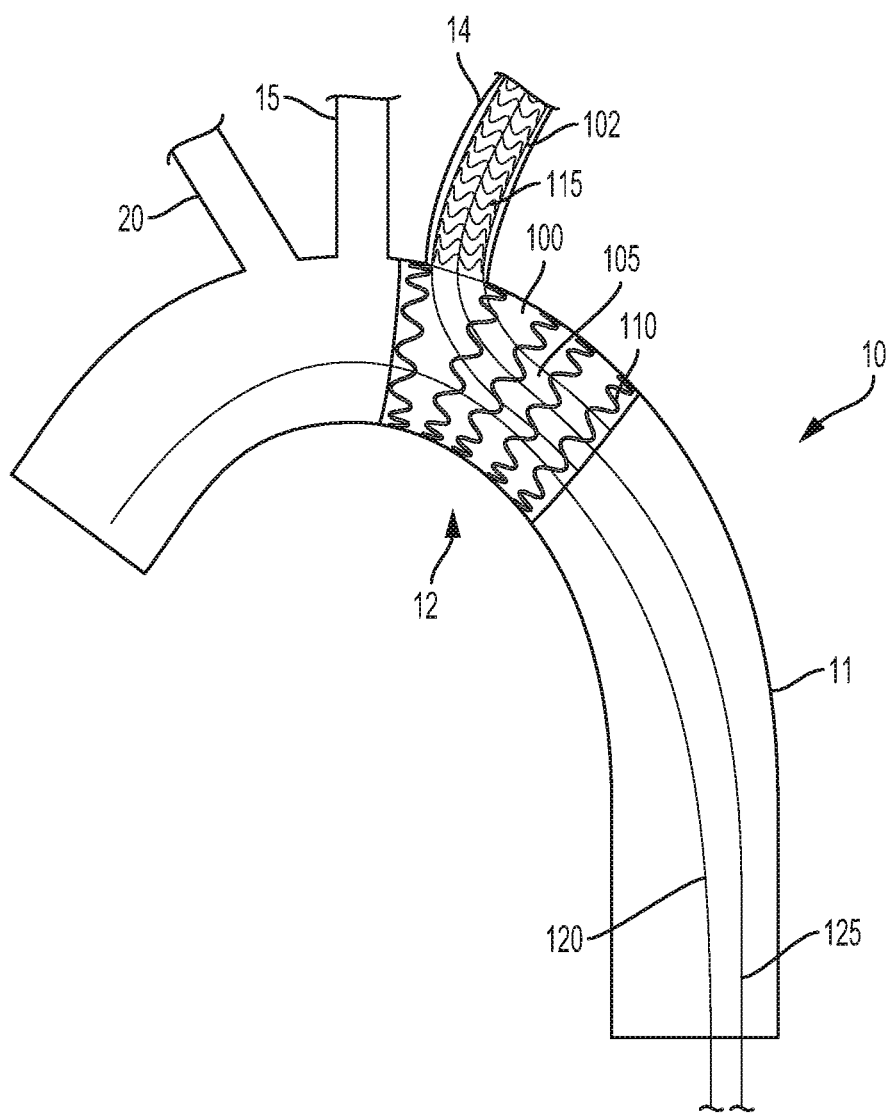
FIG. 2B shows the endovascular system of FIG. 2A deployed in an aortic arch in accordance with an embodiment.

FIG. 2A shows an endovascular system of the present disclosure in accordance with an example embodiment, and FIG. 2B shows the endovascular system of FIG. 2A deployed in an aorta 10 of a typical human. The example of the endovascular system shown in FIGS. 2A and 2B may be delivered into an existing descending thoracic system or may be modularly added to treat additional arch vessels. Referring to FIGS. 2A and 2B, an endovascular system in accordance with various embodiments includes a channel 105 on or within a main graft body (e.g., a main tubular graft body) 100, and a branch portion 102 that is received in and extends through at least a portion of the channel 105. Throughout this disclosure, the term "branch portion" refers to a branch graft or a branch stent graft. In FIG. 2B, the main graft body 100 is shown to be deployed in the aortic arch 12 of the aorta 10 via a main guidewire 120, and the branch portion 102 is shown to be deployed in the left subclavian artery 14 via a branch guidewire 125.

In various embodiments, the branch portion 102 may exit the channel 105 at any suitable location within the length of the main graft body 100. For example, the branch 102 may exit the channel 105 at a location on the main graft body 100 that is set back from a most proximal end of the main graft body 100 (e.g., as shown in FIGS. 2A and 2B), or the branch portion 102 may extend from the most proximal end of the main graft body 100. In some embodiments, the branch portion 102 (and channel 105) may extend partially along a length of the main graft body 100, but in other embodiments, the branch portion 102 (and the channel 105) may extend along an entirety of the main graft body 100. In some embodiments, the branch portion 102 may be in fluid connection with a main lumen of the main graft body 100.

In various embodiments, the branch portion 102 includes a plurality of branch stent structures 115. The branch stent structures 115 may exert a radial force on the channel 105 and/or stent structures 110 that is sufficient to keep the branch portion 102 open within the channel 105, when the branch portion 102 is deployed in the channel 105. For example, in some embodiments, the channel 105 may be cannulated (e.g., pre-cannulated) with the branch guidewire 125, and may be configured to be in a flat or closed state. Accordingly, if a user (e.g., a physician or surgeon) determines that the branch portion 102 will be deployed, the user can deploy the branch portion 102 through the channel 105 via the branch guidewire 115, and the branch portion 102 exerts a radial force on the channel 105 and/or stent structures 110 to remain open when deployed in the channel 105. In various embodiments, the entire channel 105 could be used to receive the branch portion 102, or any desirable portion of the channel 105 could be used for insertion of the branch portion 102. On the other hand, if the user determines that the branch portion 102 will not be deployed, the user may simply remove the branch guidewire 125 from the channel 105, and the channel 105 will remain flat or in a closed state.

Figure 3A:
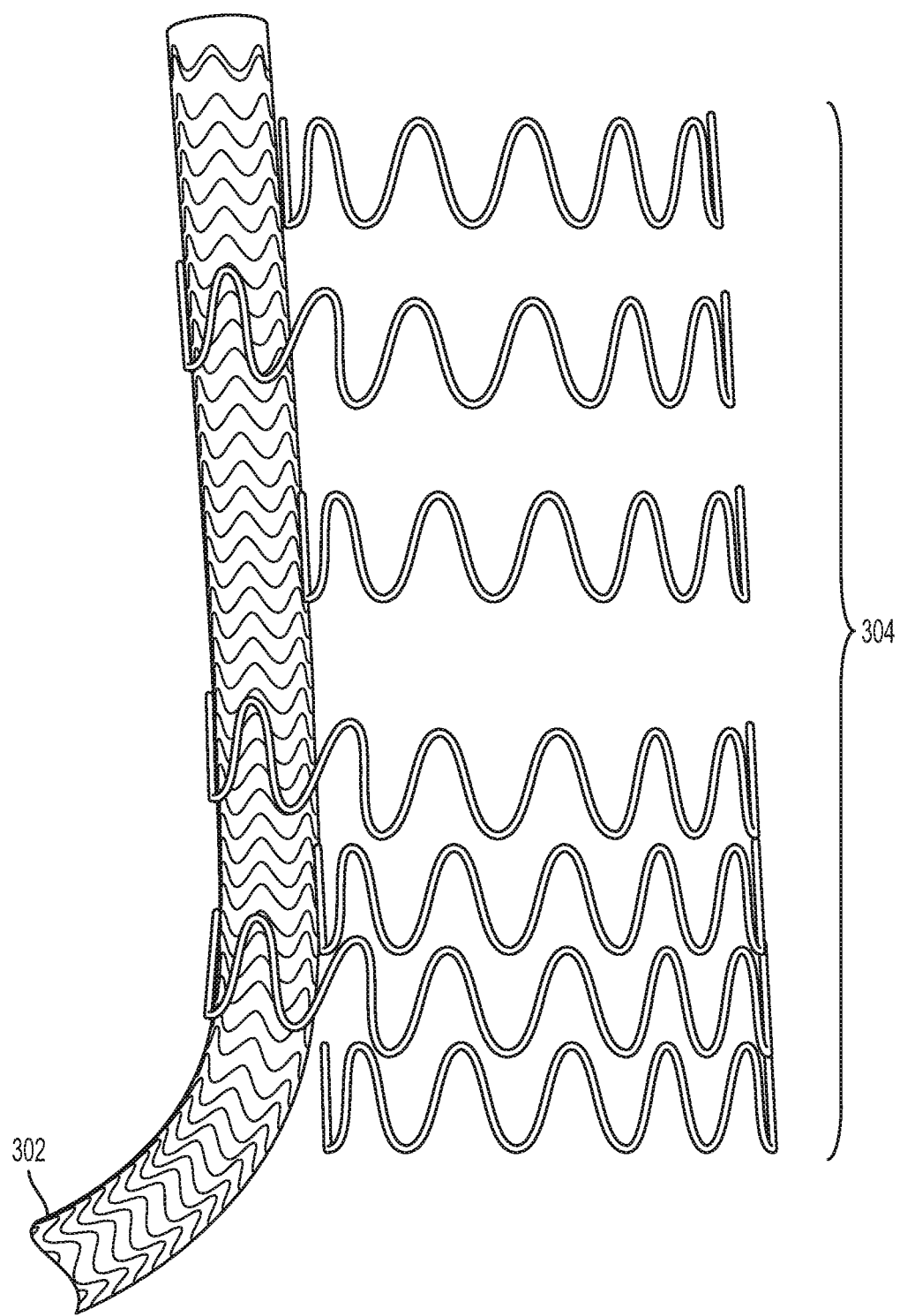
FIGS. 3A, 3B, and 3C are diagrams illustrating manners in which a branch stent graft is structurally arranged with respect to a stent structure of a main stent graft, according to various embodiments.
Figure 3B:
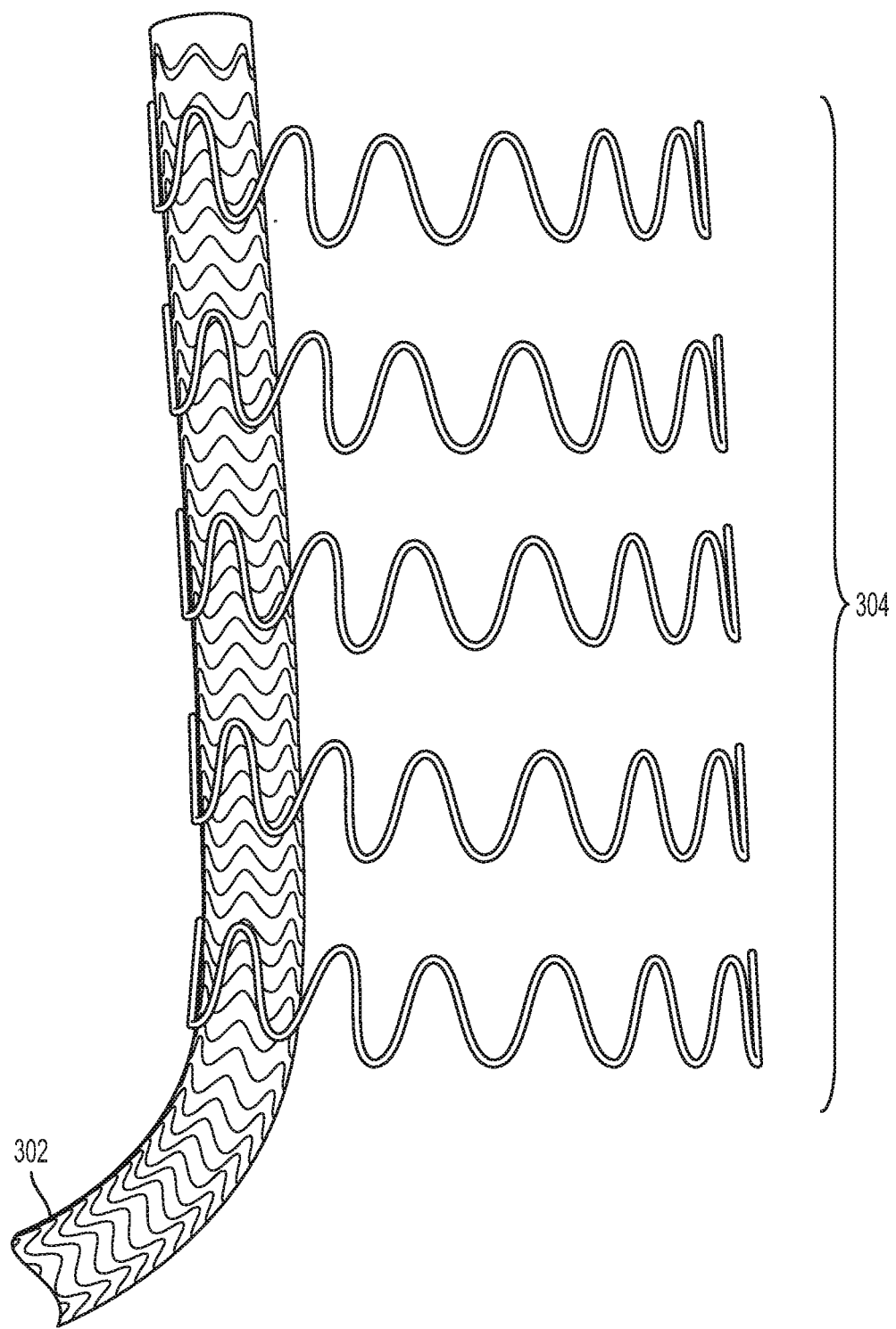
Figure 3C:
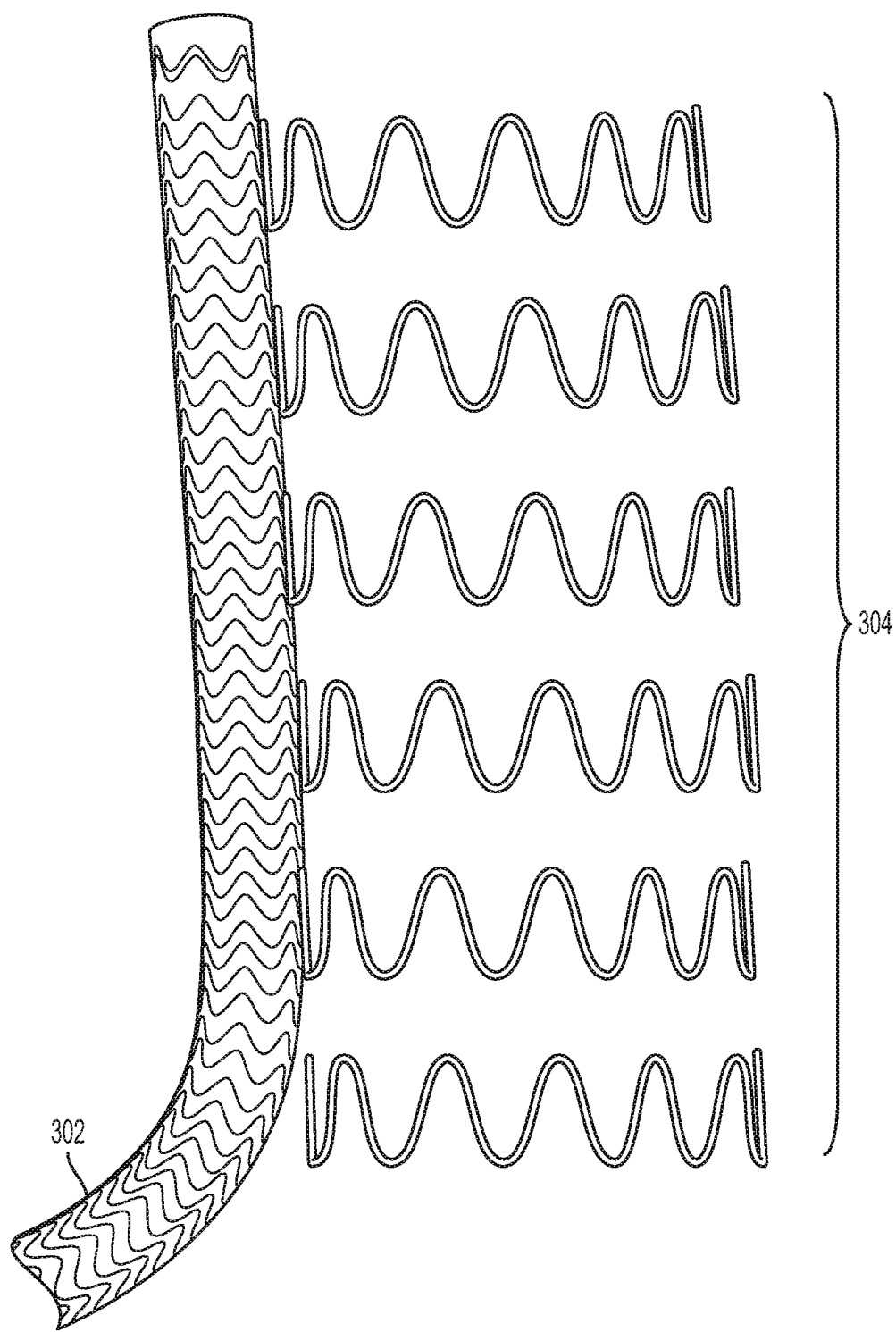

In various embodiments, the main graft body 100 includes a plurality of stent structures 110 connected to or disposed within a wall of the main graft body 100. The channel 105 may be disposed on or within the wall of the main graft body 100, and may be abluminal, adluminal, weaved, or any combinations thereof, with respect to the stent structures 110 of the main graft body 100. For example, FIGS. 3A through 3C are diagrams illustrating manners in which a branch portion is structurally arranged with respect to a stent structure of a main stent graft according to various embodiments. In FIGS. 3A-3C, the graft of the main stent graft is not shown for clarity of illustration. In more detail, FIG. 3A illustrates that the branch portion 302 may be weaved with respect to the stent structure 304, FIG. 3B illustrates that the branch portion 302 may be adluminal with respect to the stent structure 304, and FIG. 3C illustrates that the branch portion 302 may be abluminal with respect to the stent structure 304. In some embodiments, when the branch portion 302 is woven between stents of the stent structure 304 (e.g., as shown in FIG. 3A), the stent structure 304 provides sealing and anchoring of the branch portion 302. In various embodiments, the stent structure 304 exerts a radial force on the channel through which the branch portion 302 extends, and thus, if the branch portion 302 is not deployed or used, then the channel can remain closed due to the stent structure 304 (e.g., the shape retention properties of the stent structures 304), arranged in the main stent graft.

Figure 4A:
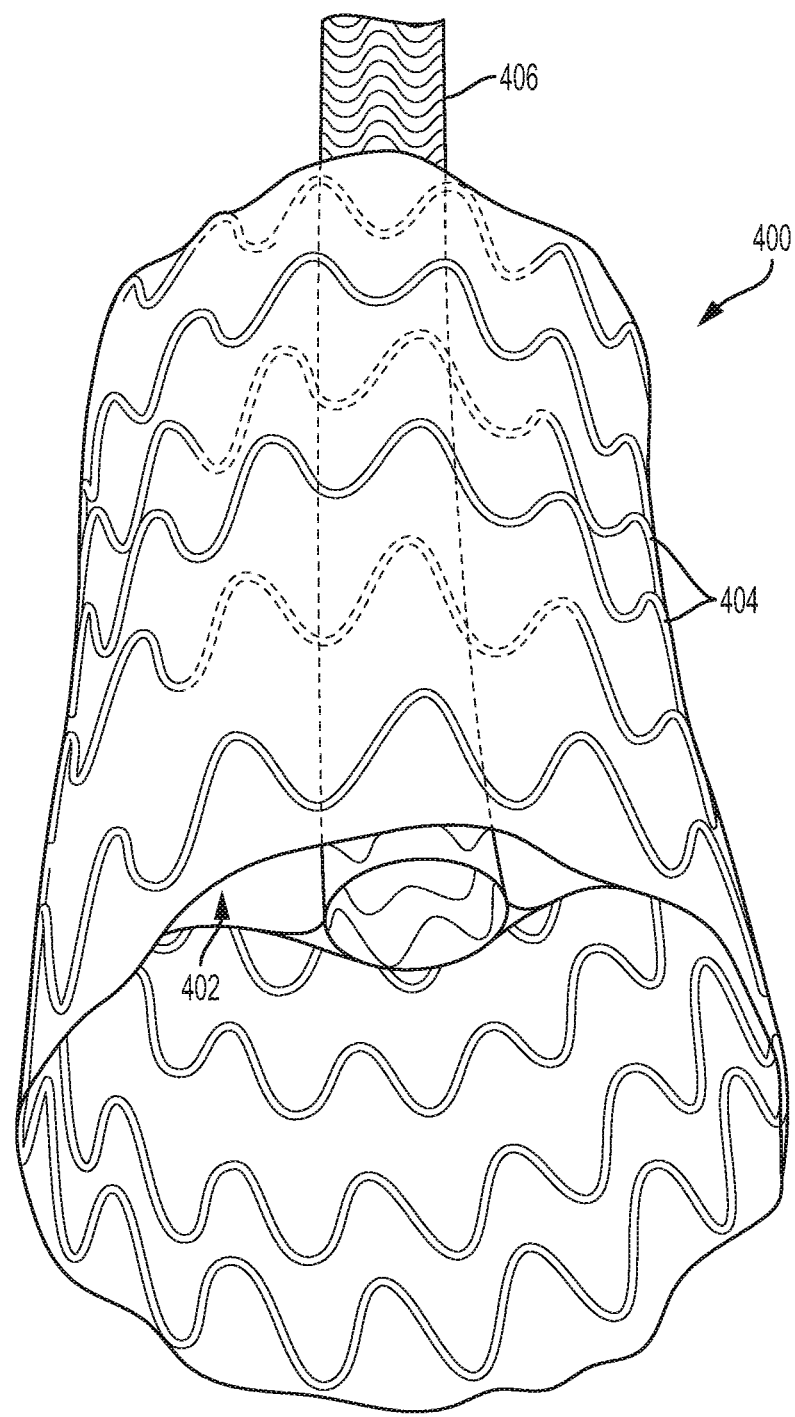
FIGS. 4A, 4B, and 4C show an example of an endovascular system according to an embodiment.
Figure 4B:
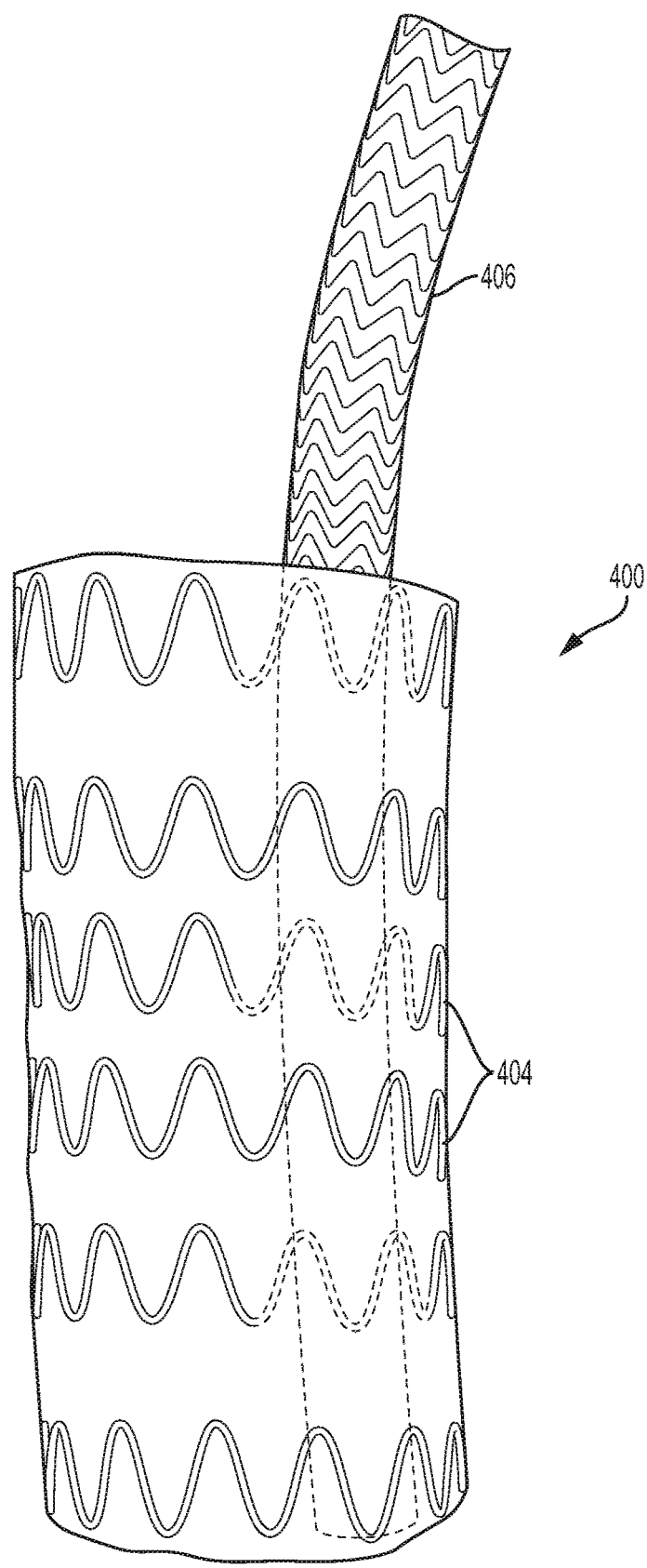
Figure 4C:
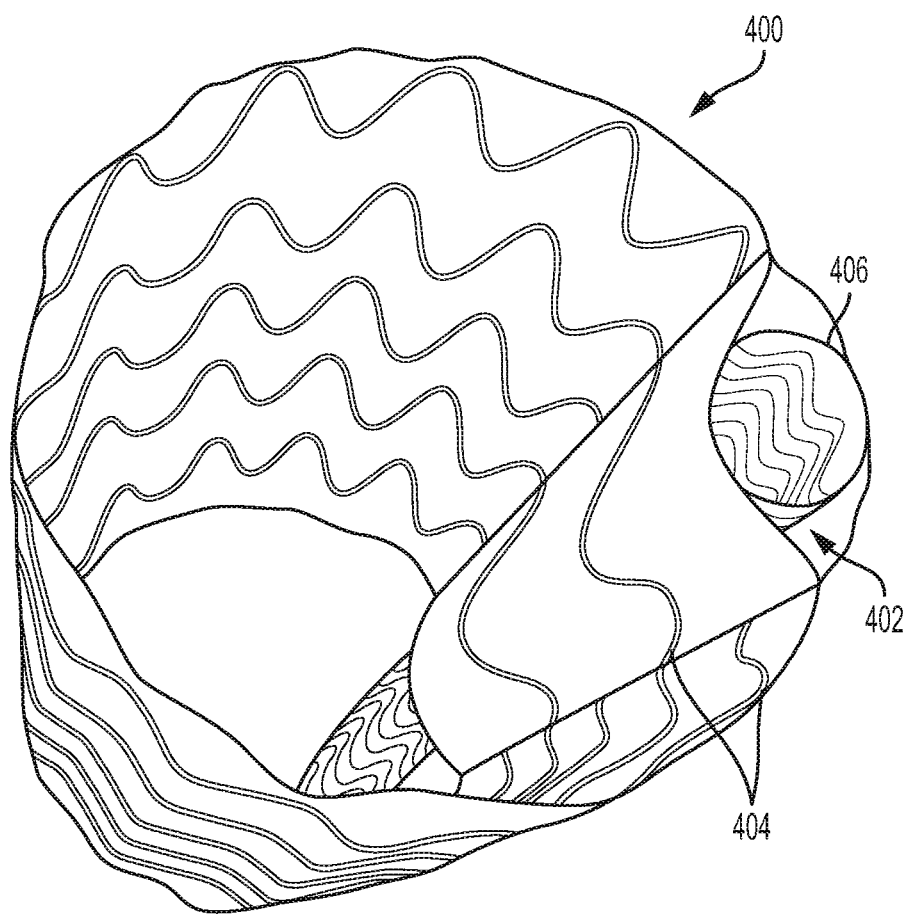

FIGS. 4A through 4C show an example of the endovascular system according to an embodiment. More specifically, FIG. 4A shows a perspective view of the endovascular system, FIG. 4B shows a side view of the endovascular system, and FIG. 4C shows a perspective view inside a main lumen of the endovascular system. The endovascular system of FIGS. 4A through 4C incorporates the weaving of a channel 402 through a stent structure 404 of a main body stent graft 400. The channel 402 is shown to be entirely located adlumially on a wall of the main body stent graft 400. However, the present disclosure is not limited thereto, and in other embodiments, for example, the channel 402 may be entirely located abluminally on the wall of the main body stent graft 400, or a portion of the channel 402 may be located abluminally on the wall of the main body stent graft 400 while another portion of the channel 402 may be located adluminally on the wall of the main body stent graft 500. In the embodiment of FIGS. 4A through 4C, a branch portion 406 is shown as extending entirely through a passageway of the channel 402 and exiting from an end (e.g., a most proximal end) of the main body stent graft 400. The branch portion 406 is woven internally into the wall and through the stent structure 404 of main body stent graft 400 via the channel 402.

FIGS. 5A through 5E show examples of forming a channel on or within a main graft body, according to various embodiments. According to various embodiments, a main stent graft body 500 is formed with various layers during a manufacturing process. Some of the layers include, for example, a plurality of Polytetrafluoroethylene (PTFE) layers that form the inner layers of the main graft body, stent structures that are disposed on the inner layers, and additional PTFE layers disposed on the stent structures to form the outer layers of the main graft body. The main stent graft body 500 is baked or heated to fuse the PTFE layers with each other, encapsulating the stent structures within the main graft body. According to various embodiments, one or more channels are formed on or within the wall of the main graft body by using an insulator sheet 502 during the manufacturing process.

Figure 5A:
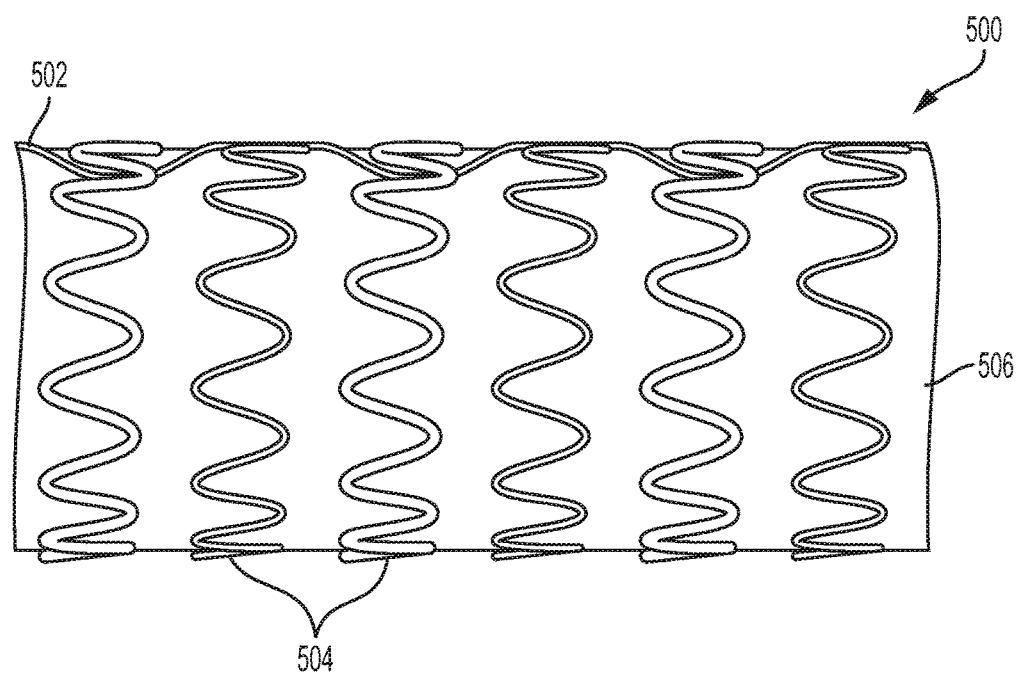
FIGS. 5A, 5B, 5C, 5D, and 5E show examples of forming a channel on or within a main body graft, according to various embodiments.
Figure 5B:
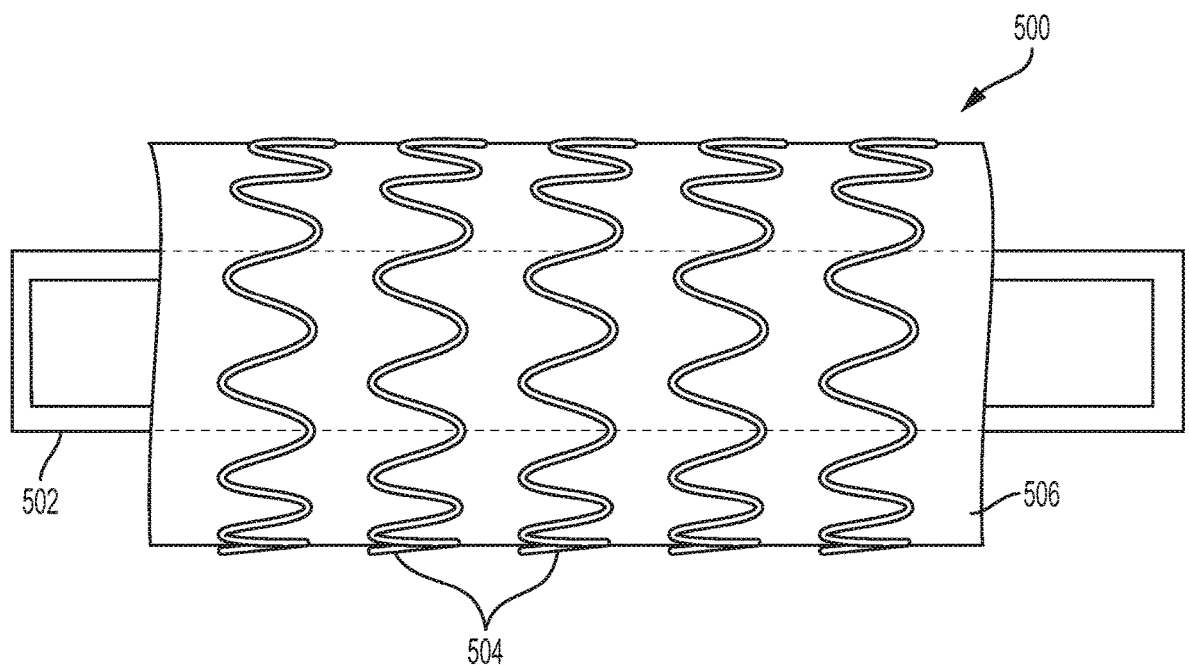
Figure 5C:
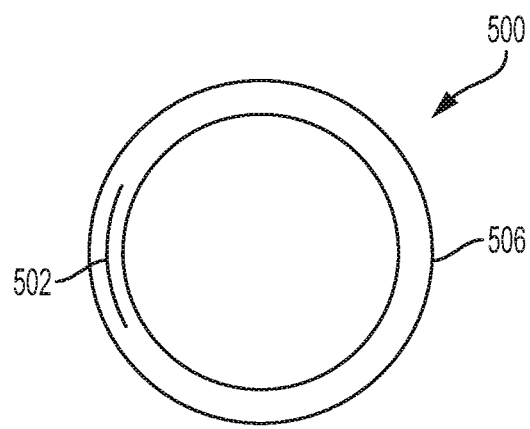

In one embodiment, referring to FIG. 5A, the insulator sheet 502 may be weaved through the stent structure 504 during the manufacturing process of the main stent graft body 500. For example, after weaving the insulator sheet 502 through the stent structure 504, the outer layers of PTFE may be formed on the stent structure 504 and the insulator sheet 502. Then, the main stent graft body 500 may be baked or heated to fuse the inner and outer PTFE layers together, encapsulating the stent structures 504 and the insulator sheet 502 therein. For example, as shown in FIG. 5C, which is a cross-section of the main body stent graft 500, the insulator sheet 502 is encapsulated within the layers of PTFE forming the main graft body 506. Afterwards, the insulator sheet 502 may be removed to form a channel that is weaved through the stent structure 504. In another embodiment, referring to FIG. 5B, an adluminal channel may be formed by disposing the insulator sheet 502 to be adluminal with respect to the stent structure 504. Similarly, in another embodiment, to form an abluminal channel, the insulator sheet 502 may be disposed to be abluminal with respect to the stent structure 504. However, the present disclosure is not limited to the foregoing examples, and a channel that is weaved, adluminal, abluminal, or any combination thereof may be formed in the manners described.

Figure 5D:
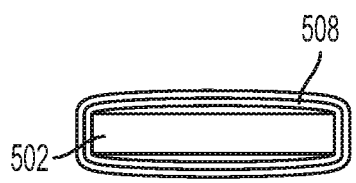
Figure 5E:
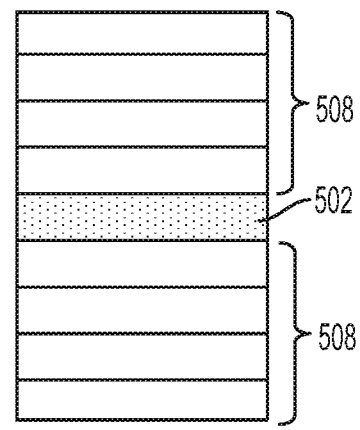

In various embodiments, the insulator sheet 502 may be formed of any suitable polymer or polymide having sufficiently high melting point and insulating properties. For example, the insulator sheet 502 may be formed of polyoxydiphenylene pyromellitimide (Kapton®). However, the present disclosure is not limited thereto, for example, the insulator sheet 502 may be formed of any suitable material, for example, such as glass, metal, or thermal plastic (e.g., polyoxybenzylmethyleneglycolanhydride or Bakelite). As shown in FIGS. 5D and 5E, in some embodiments, the insulator sheet 502 may be wrapped or otherwise covered with layers of PTFE 508 surrounding the insulator sheet 502. The layers of PTFE 508 may form a passageway for the channel through which the branch portion is received, and may reinforce the channel while creating separation between the branch portion (when received in the channel) and the stent structure 504 of the main body stent graft 500. For example, when the main body stent graft 500 is heated or baked during a manufacturing process, the layers of PTFE 508 that are wrapped around the insulator sheet 502 may fuse together with the layers of PTFE that form the main body graft 506. Thus, when the insulator sheet 502 is removed, the passageway is formed for the channel by the layers of PTFE 508 that are fused together with the PTFE layers forming the main body graft 506.

Figure 6A:
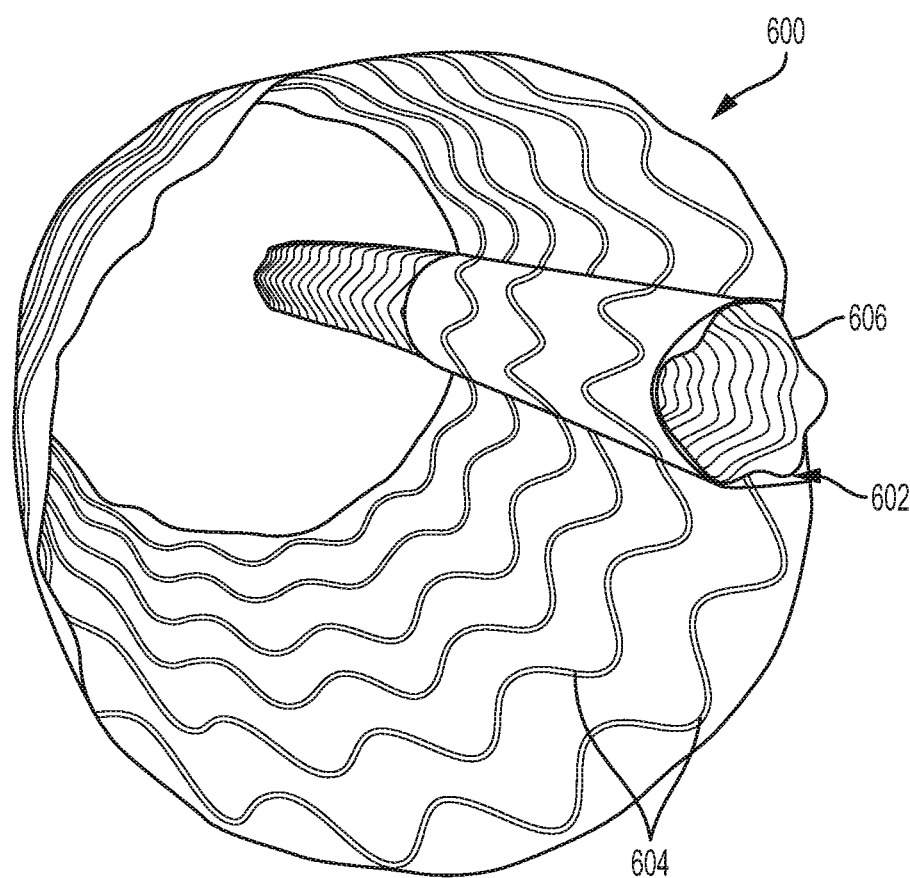
FIGS. 6A and 6B show examples of an endovascular system according to another embodiment.
Figure 6B:
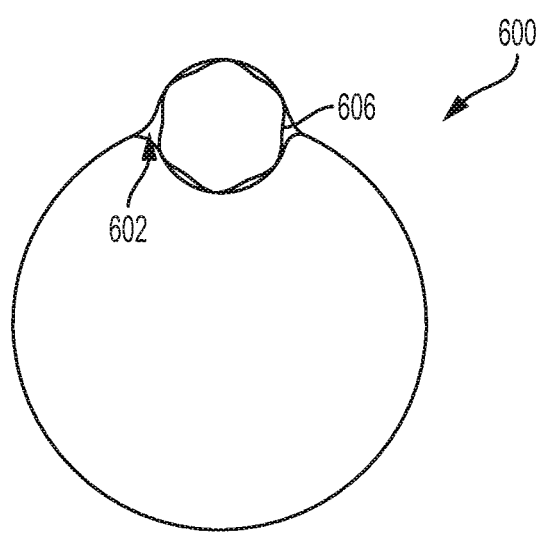

FIGS. 6A and 6B show examples of an endovascular system according to another embodiment. More specifically, FIG. 6A shows a perspective view inside a main lumen of the endovascular system, and FIG. 6B shows a cross-section of the endovascular system. The endovascular system of FIGS. 6A and 6B incorporates the weaving of a channel 602 through a stent structure 604 of a main body stent graft 600. In FIG. 6A, the channel 602 is shown to be entirely located adlumially on a wall of the main body stent graft 600. In FIG. 6B, the channel 602 is shown to be partially adluminal (e.g., a bottom hemisphere of the channel) and partially abluminal (e.g., a top hemisphere of the channel). However, the present disclosure is not limited thereto, and in other embodiments, for example, the channel 602 may be entirely located abluminally on the wall of the main body stent graft 600, or a segment of the channel 602 may be located abluminally on the wall of the main body stent graft 600 while another segment of the channel 602 may be located adluminally on the wall of the main body stent graft 600. In the embodiment of FIG. 6A, a branch portion 606 is shown as extending entirely through a passageway of the channel 602 and exiting from an end (e.g., a most proximal end) of the main body stent graft 600. The branch portion 606 is woven internally into the wall and through the stent structure 604 of main body stent graft 600 via the channel 602.

The channel 602 of the endovascular system of FIGS. 6A and 6B is different from the channel 402 of the endovascular system of FIGS. 4A through 4C in that the channel 602 is substantially tubular (or more tubular than the channel 402). A process for forming the substantially tubular channel 602 will be described in more detail with reference to FIGS. 7A and 7B. As discussed above, a main stent graft body 600 may be formed with various layers during a manufacturing process. Some of the layers include, for example, a plurality of PTFE layers that form the inner layers of the main graft body, stent structures that are disposed on the inner layers, and additional PTFE layers disposed on the stent structures to form the outer layers of the main graft body. The main stent graft body 600 is baked or heated to fuse the PTFE layers together, encapsulating the stent structures 604 within the main graft body. According to various embodiments, one or more substantially tubular channels are formed on or within the wall of the main graft body by using an insulator sheet and a plurality of separator sheets during the manufacturing process.

Figure 7A:
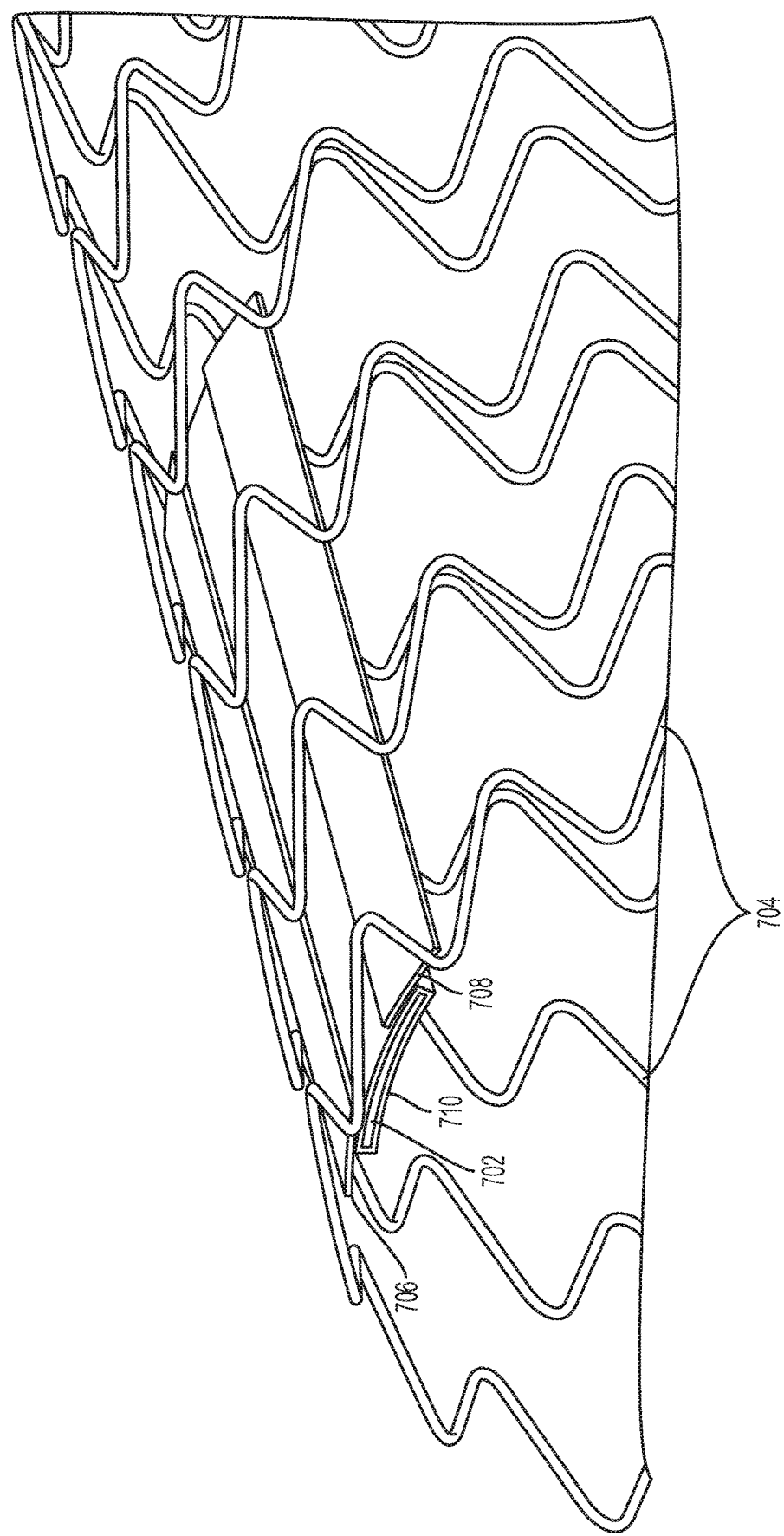
FIGS. 7A and 7B show an example of forming a substantially tubular channel on or within a main body graft, according to various embodiments.
Figure 7B:
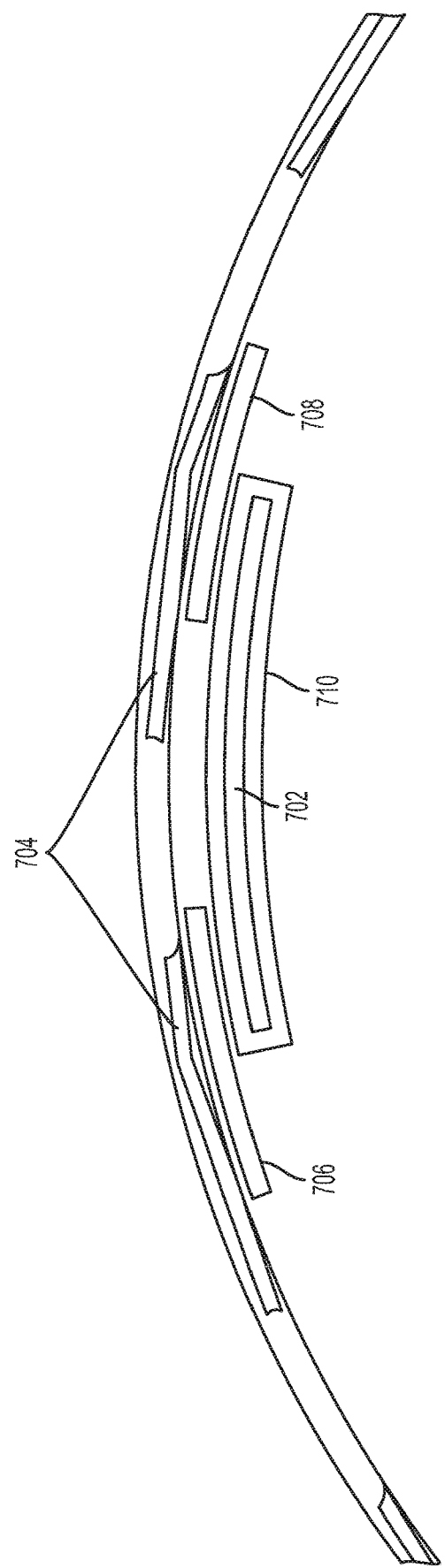

For example, referring to FIGS. 7A and 7B, an insulator sheet 702 and two or more separator sheets 706 and 708 may be weaved through a stent structure 704 during the manufacturing process of the main stent graft body. For example, the separator sheets 706 and 708 may be arranged on a side of the insulator sheet 702, while spaced apart from each other. The insulator sheet 702 and the separator sheets 706 and 708 may be weaved through the stent structure 704. In this case, the insulator sheet 702 may be wrapped or otherwise covered with layers of PTFE 710 surrounding the insulator sheet 702 in the same or substantially the same manner as discussed above with reference to FIGS. 5D and 5E. On the other hand, unlike the insulator sheet 702, the separator sheets 706 and 708 may not be wrapped or otherwise covered with layers of PTFE. In various embodiments, each of the insulator sheet 702 and the separator sheets 706 and 708 may be formed of any suitable polymer or polymide having sufficiently high melting point and insulating properties. For example, the insulator sheet 702 and the separator sheets 706 and 708 may be formed of poly-oxydiphenylene pyromellitimide (Kapton®). However, the present disclosure is not limited thereto, for example, each of the insulator sheet 702 and the separator sheets 706 and 708 may be formed of any suitable material, for example, such as a thermal plastic (e.g., polyoxybenzylmethyleneglycolanhydride or Bakelite), glass, or metal. Further, the insulator sheet 702 and the separator sheets 706 and 708 may be made of different materials from one another.

The separator sheets 706 and 708 may be spaced apart, so that a central portion of the layers of PTFE 710 is exposed between the separator sheets 706 and 708. Then, the outer layers of PTFE may be formed on the stent structure 704, the insulator sheet 702, and the separator sheets 706 and 708. Thereafter, the main stent graft body may be baked or heated to fuse the inner and outer PTFE layers together, encapsulating the stent structures 704, the insulator sheet 702, and the separator sheets 706 and 708 therein. Afterwards, the insulator sheet 702 and the separator sheets 706 and 708 may be removed, and an arch of the substantially tubular channel may be formed by using the separator sheets 706 and 708. For example, when the main body stent graft is heated or baked during a manufacturing process, the exposed central portion of the layers of PTFE 710 that are wrapped around the insulator sheet 702 may fuse together with the layers of PTFE that form the main body graft. On the other hand, the separator sheets 706 and 708 may prevent the side portions of the PTFE 710 from fusing together with the PTFE forming the main body graft, so that an arch of the substantially tubular channel may be formed. Thus, when the insulator sheet 702 and the separator sheets 706 and 708 are removed, the substantially tubular passageway that is weaved through the stent structures 704 is formed for the substantially tubular channel.

Accordingly, the layers of PTFE 710 may form a substantially tubular passageway for the channel through which the branch portion is received, and may reinforce the channel while creating separation between the branch portion (when received in the channel) and the stent structure 704 of the main body stent graft. In another embodiment, an adluminal channel may be formed by disposing the insulator sheet 702 and the separator sheets 706 and 708 to be adluminal with respect to the stent structure 704. Similarly, in another embodiment, to form an abluminal channel, the insulator sheet 702 and the separator sheets 706 and 708 may be disposed to be abluminal with respect to the stent structure 704. However, the present disclosure is not limited to the foregoing examples, and a substantially tubular channel that is weaved, adluminal, abluminal, or any combination thereof may be formed in the manners described.

Figure 8:
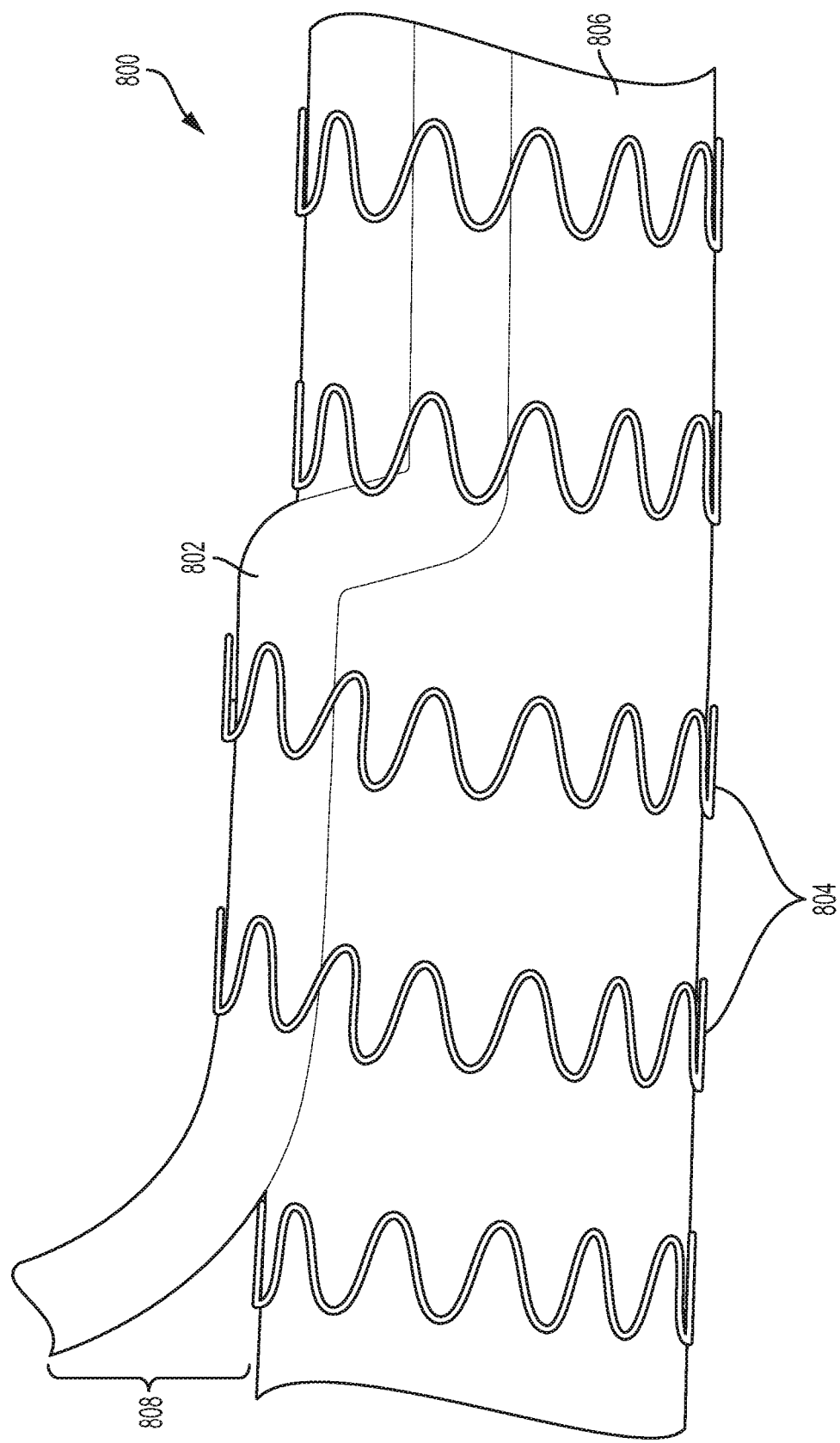
FIG. 8 shows an endovascular system in accordance with an embodiment.

FIG. 8 shows an endovascular system in accordance with various embodiments. Referring to FIG. 8, a channel 802 may be substantially adluminal with respect to a stent structure 804, and may have an adluminal segment and an abluminal segment with respect to a main body graft 806. Accordingly, a portion of the passageway of the channel 802 may run within an interior of the main lumen of the main stent graft body, and a portion of the passageway of the channel 802 may run exterior to the main lumen. In some embodiments, an end portion of the channel 802 (e.g., a proximal end) may include a branch support flap 808 that freely extends from the exterior of the main body graft 806. In some embodiments, the branch support flap may extend from the exterior of the main graft body 806 at any suitable location that is set back from a most proximal end of the main stent graft, or may extend from within the main lumen at the most proximal end of the main stent graft. The branch support flap 808 may provide additional support for a branch portion received therein, and may be flexible and moveable independent from the main body graft 806.

Figure 9:
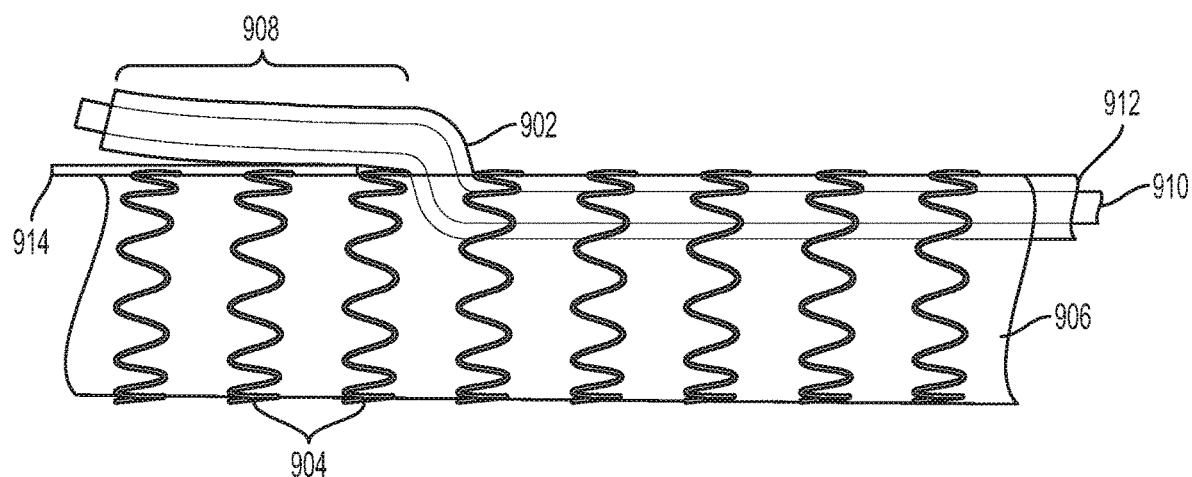
FIG. 9 shows an example of forming an abluminal branch support flap, according to an embodiment.

FIG. 9 shows an example of forming an abluminal branch support flap, according to an embodiment. Referring to FIG.

9, a channel 902 is formed to be substantially adluminal with respect to a stent structure 904, and includes an abluminal body support flap 908. Thus, a passageway of the channel 902 runs from an interior of the main body graft 906 to an exterior thereof through the abluminal body support flap 908. To form the abluminal body support flap 908, an insulator sheet 910 having a bent portion therein, or any suitable desired shape for the resulting channel, is wrapped or otherwise covered in layers of PTFE 912. The wrapped insulator sheet 910 is inserted through the main body graft 906 between corresponding stent structures 904, so that a segment of the wrapped insulator sheet 910 is adluminal with respect to some of the stent structures 904, and a segment of the wrapped insulator sheet 910 that forms the body support flap 908 is abluminal with respect to the main body stent graft. A separator sheet 914 is arranged between the main body stent graft and the segment of the wrapped insulator sheet 910 that forms the body support flap 908 to provide separation of the body support flap 908 from the main body graft 906. The assembly is then heated or baked to fuse the layers of PTFE 912 with the PTFE layers of the main body graft 906. In this case, the separator sheet 914 prevents the body support flap 908 from fusing to the PTFE layers of the main body graft 906. The separator sheet 914 and the insulator sheet 910 is then removed, resulting in the channel 902 that is substantially adluminal with respect to the stent structure 904 and having the abluminal body support flap 908 that is moveable independent from the main body graft 906.

In various embodiments, each of the insulator sheet 910 and the separator sheet 914 may be formed of any suitable polymer or polymide having sufficiently high melting point and insulating properties. For example, the insulator sheet 910 and the separator sheet 914 may be formed of poly-oxydiphenylene pyromellitimide (Kapton®). However, the present disclosure is not limited thereto, for example, each of the insulator sheet 910 and the separator sheet 914 may be formed of any suitable material, for example, such as a thermal plastic (e.g., polyoxybenzylmethyleneglycolanhydride or Bakelite), glass, or metal. Further, the insulator sheet may be made of different material from the separator sheet 914. Further, while the insulator sheet 910 is wrapped or otherwise covered by the layers of PTFE 912, the separator sheet 914 is not wrapped with layers of PTFE.

Figure 10:
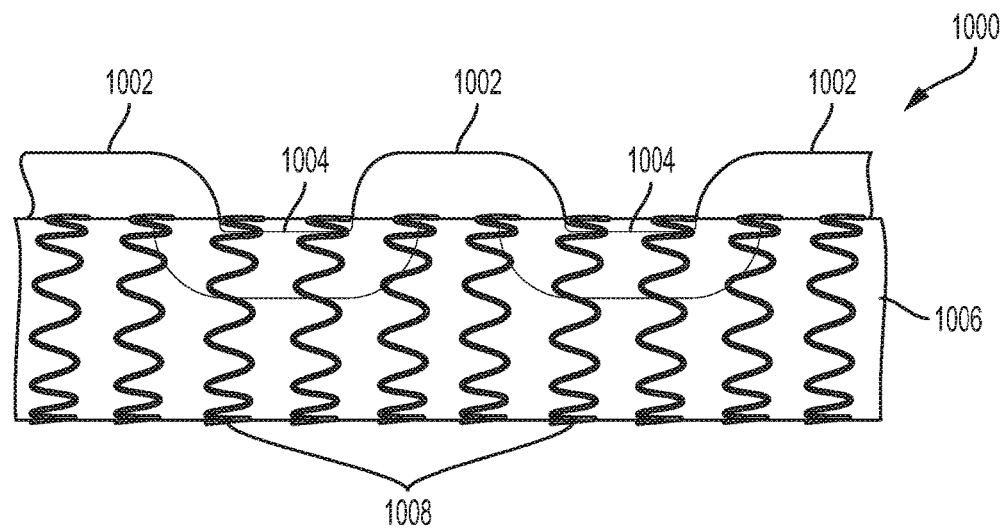
FIG. 10 shows an endovascular system in accordance with an embodiment.

In another embodiment, the body support flap 908 may be fused to the main body graft 906 by omitting the separator sheet 914 when heating or baking the assembly. In this case, the channel 902 has a segment that is adluminal to the stent structures 904 and the main body graft 906 and a segment that is abluminal to the stent structures 904 and the main body graft 906. For example, FIG. 10 shows an endovascular system in accordance with another embodiment. Referring to FIG. 10, a main body stent graft 1000 may have a channel that is formed to have a plurality of abluminal segments 1002 and a plurality of adluminal segments 1004. The channel may be formed by weaving an insulator sheet that is wrapped or otherwise covered by layers of PTFE through a main body graft 1006 between corresponding stent structures 1008. The wrapped insulator sheet may have a shape corresponding to the desired shape of the resulting channel. The assembly is then heated or baked so that the layers of PTFE of the wrapped insulator sheet can fuse together with the PTFE layers of the main body graft 1006. The insulator sheet is removed thereafter, resulting in the channel having the plurality of abluminal segments 1002 and the plurality of adluminal segments 1004.

Figure 11:
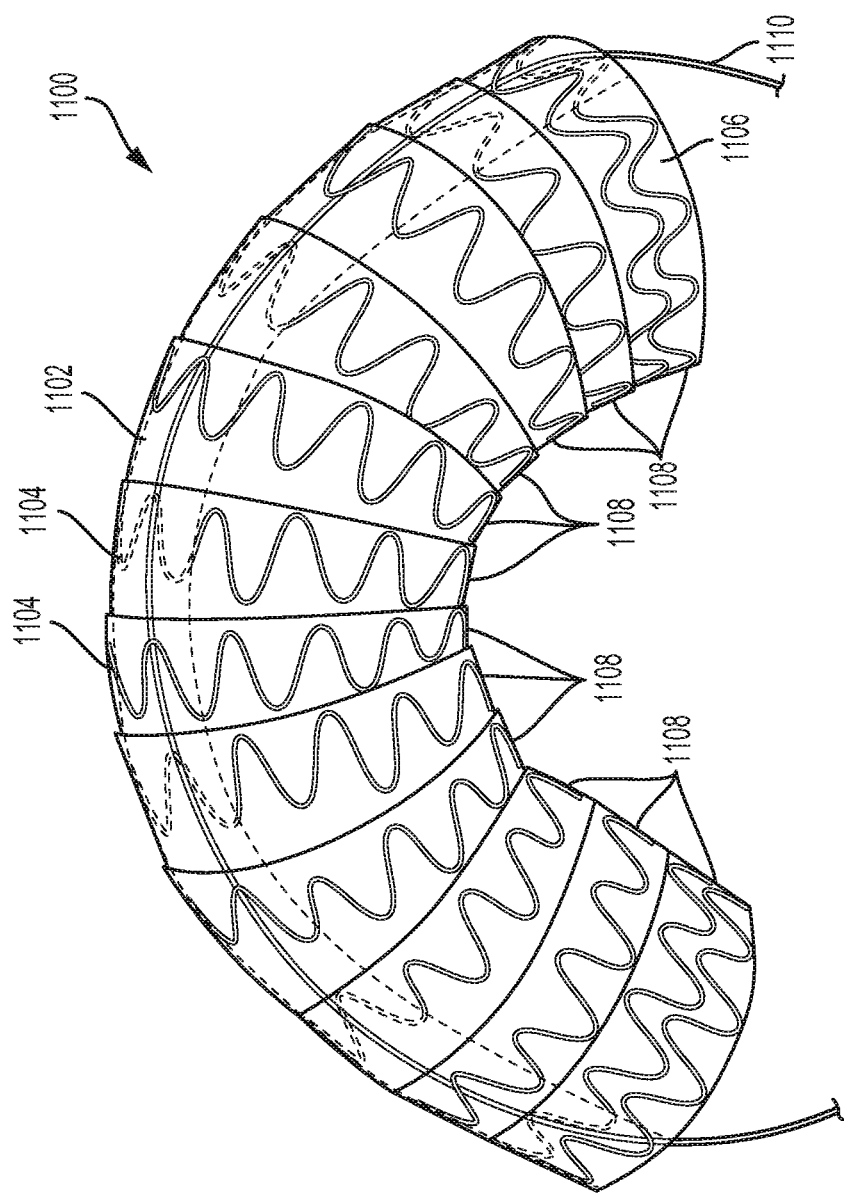
FIG. 11 shows an endovascular system in accordance with an embodiment.

FIG. 11 shows an endovascular system in accordance with an embodiment. A main body stent graft 1100 includes a channel 1102 that is weaved through stent structures 1104 on or within a main body graft 1106. The main body graft 1106 is pleated at pleated portions 1108. Each of the pleated portions 1108 may overlap with an adjacent pleated portion 1108 adluminally and/or abluminally. The pleated portions 1108 may be located at a side of the main body graft 1106 opposite the channel 1102, while a side of the main body graft 1106 including the channel 1102 may be unpleated or substantially unpleated (e.g., pleated with a slight overlap), so that a wire 1110 can be cannulated in the channel 1102 for delivering a branch portion into the channel 1102.

Figure 12:
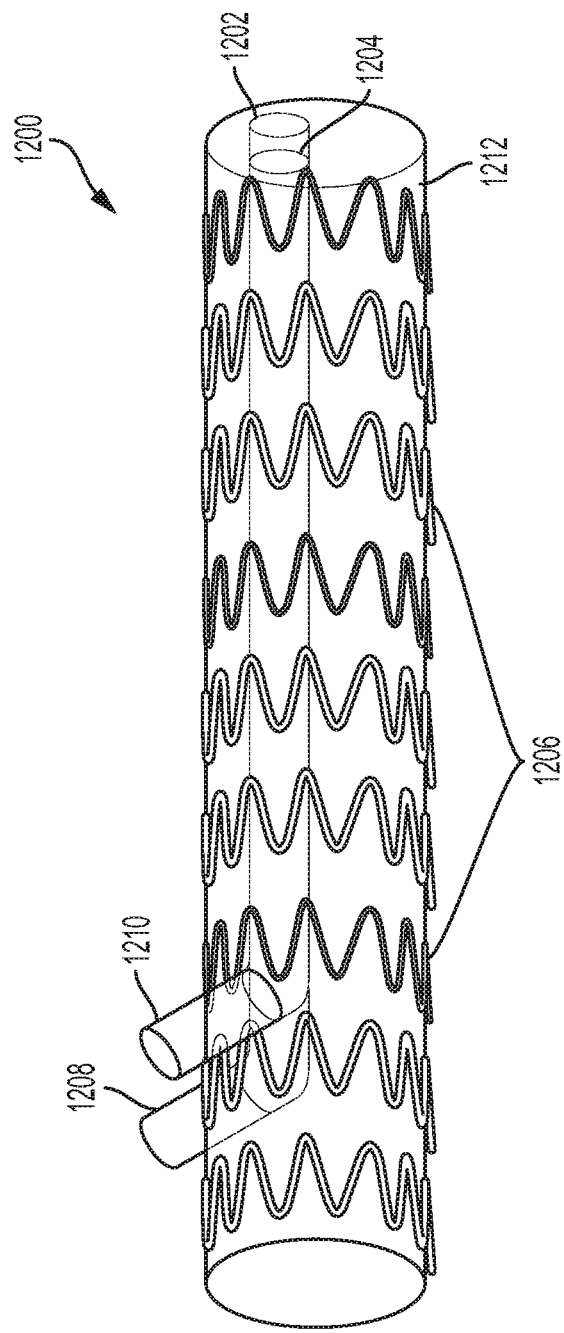
FIG. 12 shows an endovascular system having two or more channels in a main body stent graft, in accordance with an embodiment.

FIG. 12 shows an endovascular system having two or more channels in a main body stent graft in accordance with an embodiment. Referring to FIG. 12, a main body stent graft 1200 includes a first channel 1202 and a second channel 1204. Each of the first and second channels may be formed to be substantially adluminal with respect to a stent structure 1206, but the present disclosure is not limited thereto, and in other embodiments, at least one of the first and second channels 1202 and 1204 may be weaved or abluminal with respect to the stent structure 1206. The first channel 1202 includes an a first abluminal body support flap 1208, and the second channel 1204 includes a second abluminal body support flap 1210. Thus, a first passageway of the first channel 1202 runs from an interior of the main body graft 1212 to an exterior thereof through the first abluminal body support flap 1208. A second passageway of the second channel 1204 runs from the interior of the main body graft 1212 to the exterior thereof through the second abluminal body support flap 1210. Each of the first and second channels 1202 and 1204 including the first and second abluminal body support flaps 1208 and 1210 may be formed in the same or substantially the same manner as discussed above with reference to FIG. 9, and thus, detailed description thereof will not be repeated. In another embodiment, each of the first and second abluminal body support flaps 1208 and 1210 may be omitted.

Figure 13A:
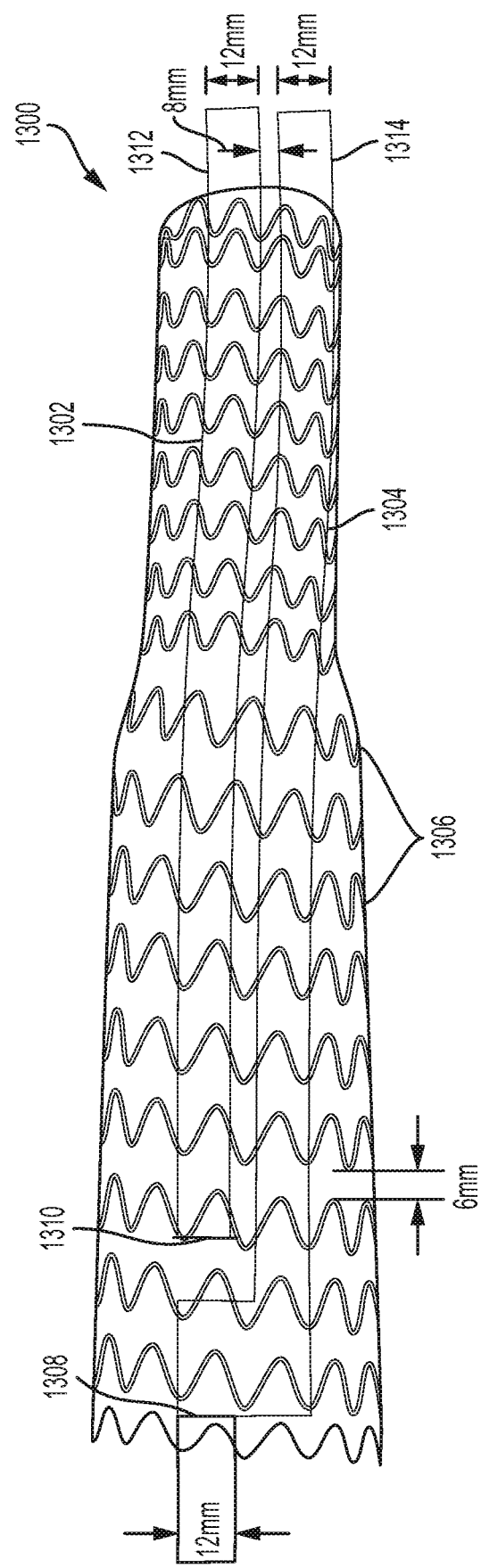
FIGS. 13A, 13B, and 13C show an endovascular system having two or more channels in a main body stent graft, in accordance with an embodiment.
Figure 13B:
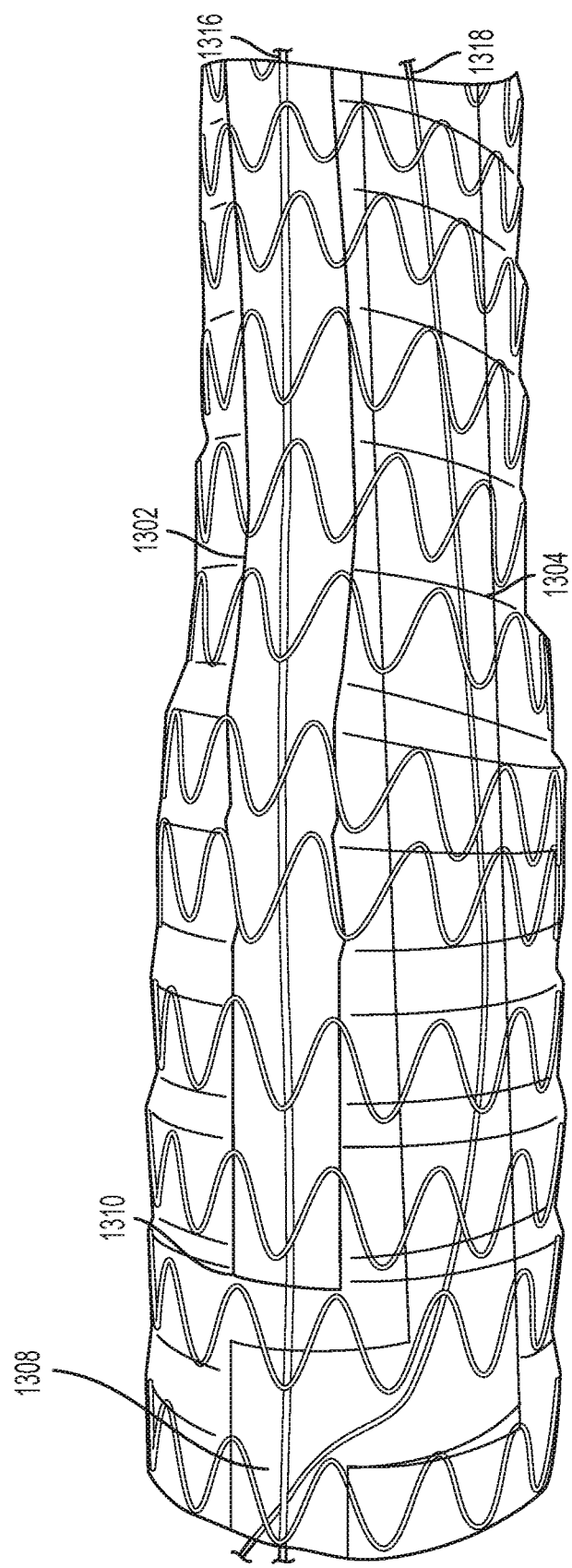
Figure 13C:
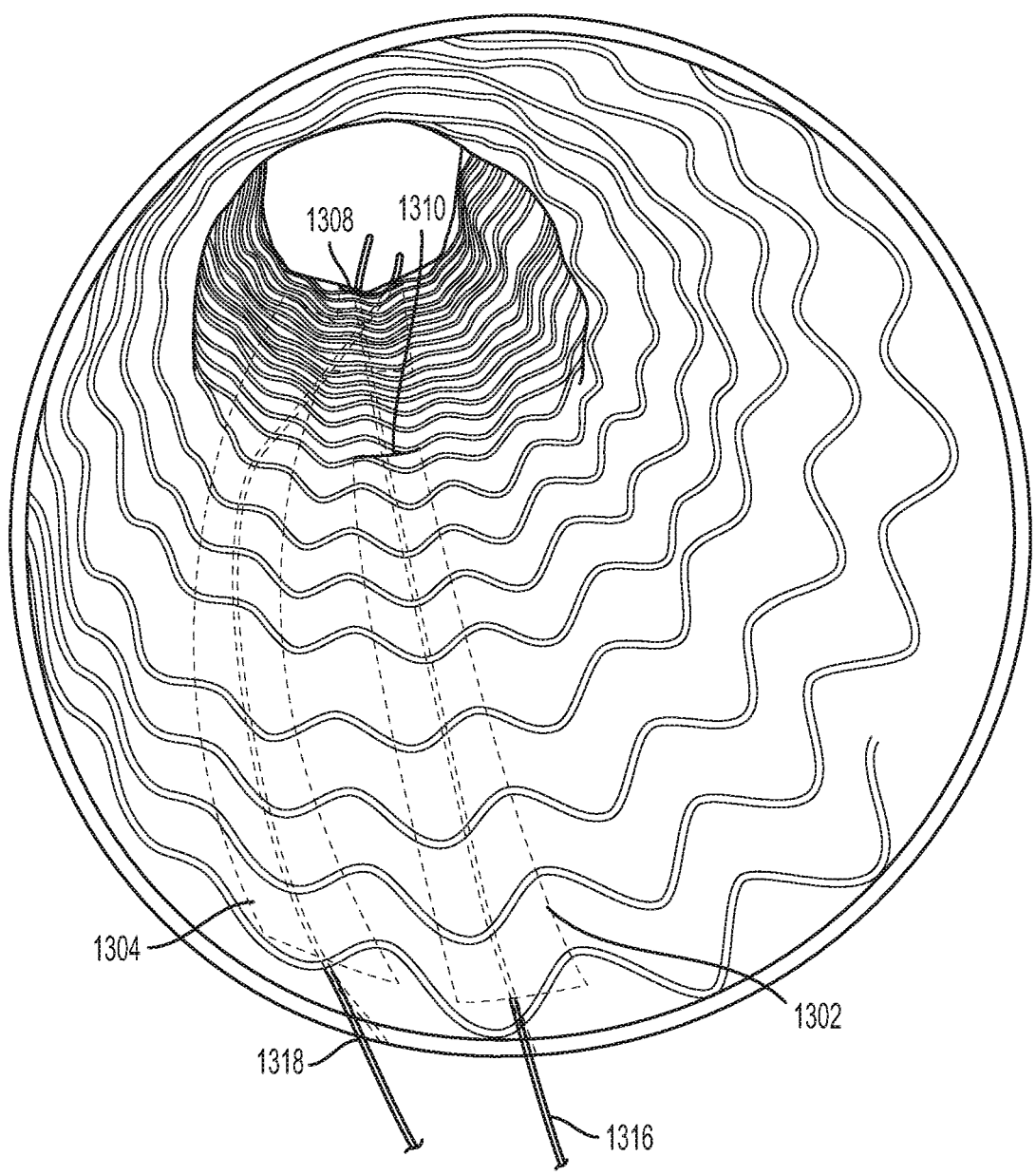

FIGS. 13A through 13C show an endovascular system having two or more channels in a main body stent graft in accordance with another embodiment. Referring to FIGS. 13A through 13C, a main body stent graft 1300 may include a plurality of channels, for example, a first channel 1302 and a second channel 1304. Each of the plurality of channels 1302 and 1304 may be weaved, abluminal, adluminal, or any combination thereof, with respect to a stent structure 1306. According to various embodiments, a passageway of the plurality of channels 1302 and 1304 may be variously formed to have one or more bends therein. For example, as shown in FIGS. 13A through 13C, the first channel 1302 has a passageway that is substantially straight, and the second channel 1304 has a passageway that includes a bend therein. Accordingly, when a branch portion is inserted in a corresponding channel, the branch portion may have sufficient flexibility to follow one or more bends of the passageway of the corresponding channels. In this manner, an exit location of the corresponding branch portion from the main body stent graft 1300 may correspond to the passageway of the corresponding channel. For example, as shown in FIGS. 13A through 13C, the exit location 1308 of the second channel 1304 may be axially aligned with the exit location 1310 of the first channel 1302, even though the first and second channels each extend across the length of the main body stent graft 1300.

In various embodiments, the passageways of each of the plurality of channels 1302 and 1304 may be formed to correspond to a shape of insulator sheets used to form the plurality of channels 1302 and 1304. For example, according to various embodiments, the main body stent graft 1300 is formed with various layers during a manufacturing process, as discussed above. During the manufacturing process a first insulator sheet 1312 and a second insulator sheet 1314 may be weaved, abluminal, adluminal, or any desired combination thereof, with respect to the stent structure 1306. The first insulator sheet 1312 may be substantially straight to form a substantially straight channel 1302, and the second insulator sheet 1314 may have a bend to form a channel 1304 with a bend. In various embodiment, if a substantially tubular channel is desired, a plurality of separator sheets may be arranged on the first and/or second channels 1302 and 1304 in the manner discussed above with reference to FIGS. 7A and 7B. In some embodiments, each of the first and second insulator sheets 1312 and 1314 may be wrapped or otherwise covered by a plurality of PTFE layers for additional channel support and to provide further separation between the branch stent structures and the stent structure 1306 of the main body graft 1300.

In various embodiments, the first and second insulator sheets 1312 and 1314 may be arranged to form the first and second channels 1302 and 1304 at any desired locations on or within the main body graft. For example, as shown in FIG. 13A, each of the first and second insulator sheets 1312 and 1314 may have a width of about 12 mm so that a channel is formed with sufficient room for receiving a corresponding branch portion. The first and second insulator sheets 1312 and 1314 may be spaced apart from each other by about 8 mm or more, to sufficiently allow the PTFE materials of the main body stent graft 1300 to fuse together between the formed channels to allow for sufficient separation and chamber formation. In addition, if a sharp (e.g., 90 degree) bend portion is formed, then the width of the insulator sheet at the bend portion may be wider than the width of the insulator sheet at the straight portion so that the passageway of the formed channel can be wide enough to allow the branch portion to bend therethrough. On the other hand, if the bend portion has a lesser angle (e.g., about 45 degrees or less), then the insulator sheet may have substantially the same width throughout. In some embodiments, the stent structure 1306 may be spaced apart from a corresponding adjacent stent structure by about 6 mm. As shown in FIGS. 13B and 13C, the first and second channels 1302 and 1304 may be cannulated with first and second guidewires 1316 and 1318, respectively, to guide corresponding branch portions to be inserted therethrough.

Figure 14A:
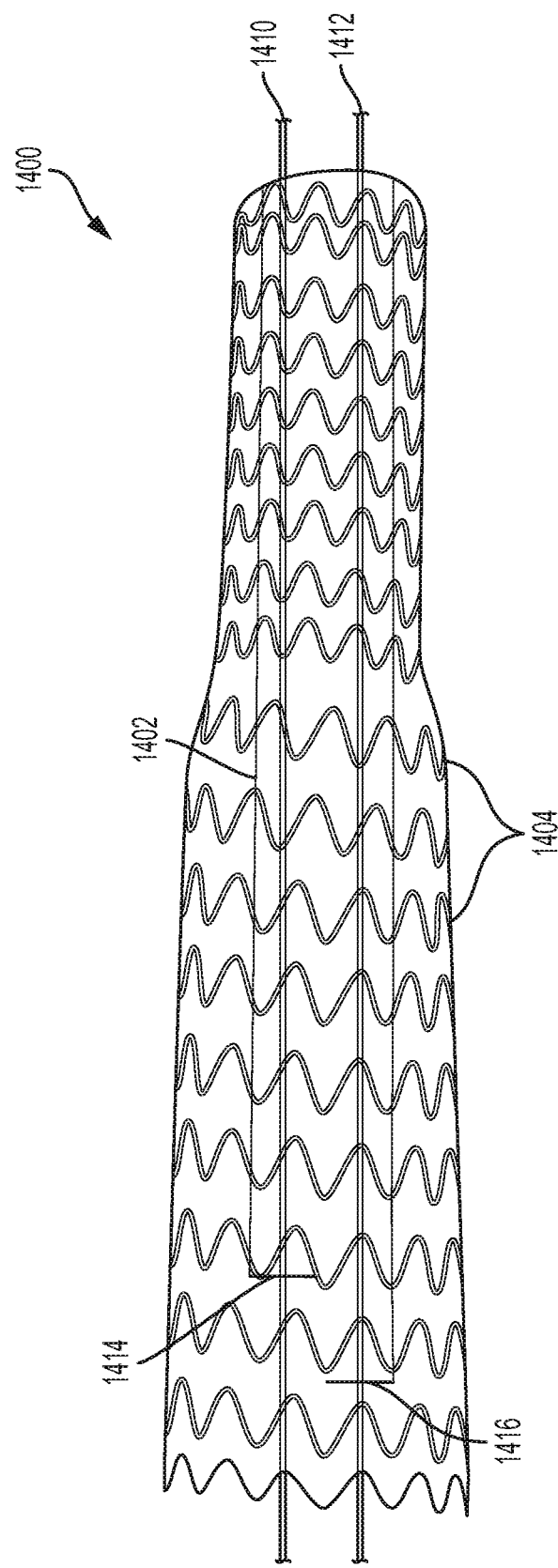
FIGS. 14A and 14B show an endovascular system having a channel in a main body stent graft that can receive two or more branch portions, in accordance with an embodiment.
Figure 14B:
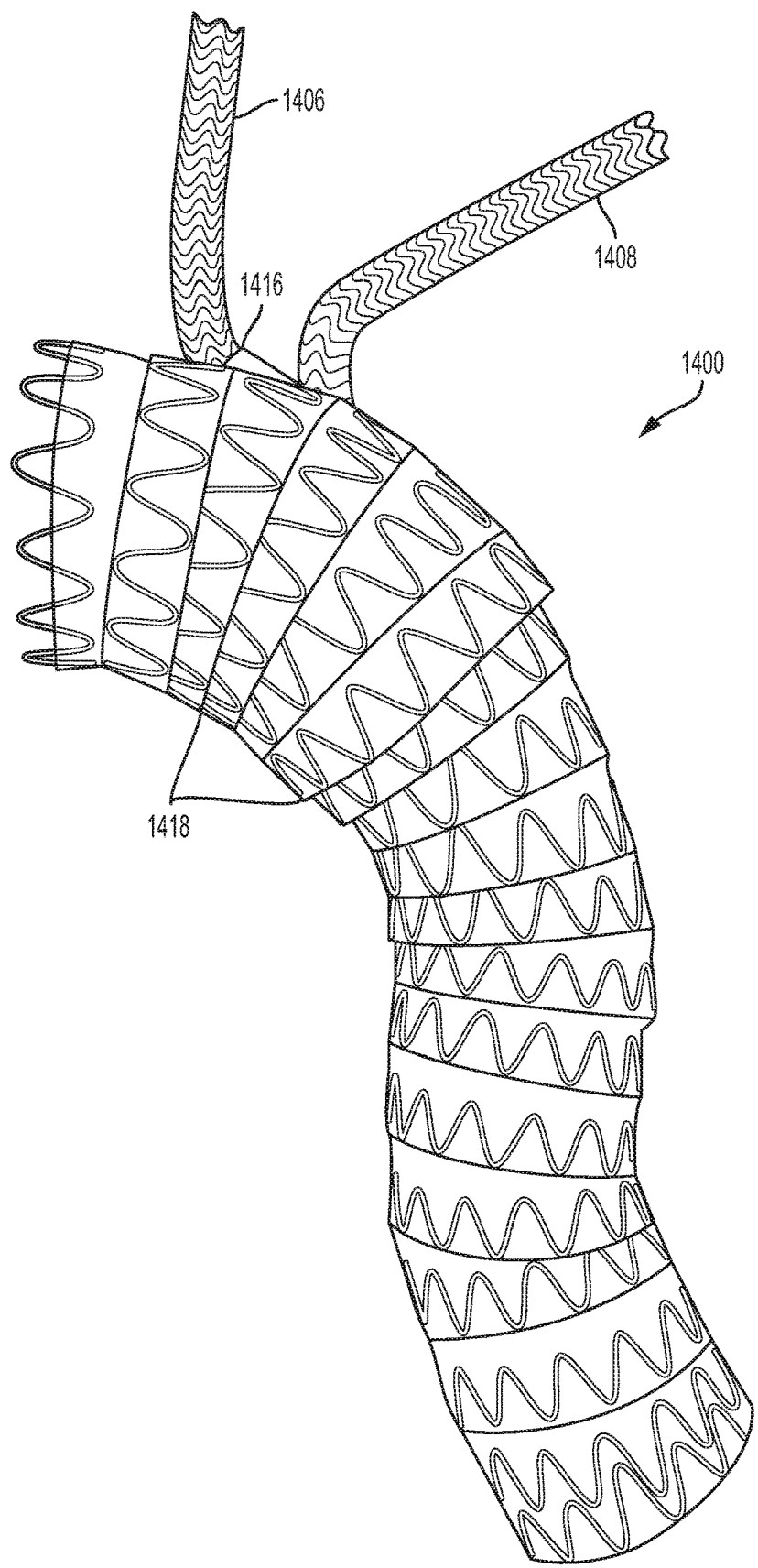

FIGS. 14A and 14B show an endovascular system having a channel in a main body stent graft that can receive two or more branch portions, in accordance with an embodiment. Referring to FIGS. 14A and 14B, a main body stent graft 1400 may include a channel 1402, which may be weaved, abluminal, adluminal, or any combination thereof, with respect to a stent structure 1404. According to an embodiment, the channel 1402 may be sufficiently wide so that two or more branch portions can be received therein. For example, as shown in FIG. 14B, the channel 1402 may receive both a first branch portion 1406 and a second branch portion 1408. Thus, the first and second branch portions 1406 and 1408 may contact each other within the channel 1402. The first and second branch portions 1406 and 1408 may be inserted into the channel 1402 via first and second guidewires 1410 and 1412, respectively, that are cannulated in the channel 1402. The first and second guidewires 1410 and 1412, and thus, the first and second branch portions 1406 and 1408, may exit the channel at different exit locations 1414 and 1416, respectively. However, the present disclosure is not limited thereto, and in other embodiments, the exit locations 1414 and 1416 may form a single exit location that spans across an entire width of the channel 1402. In some embodiments, the channel 1402 may be formed from an insulator sheet having a step portion corresponding to the exit locations 1414 and 1416. However, the present invention is not limited thereto, and the exit locations 1414 and 1416 may be cut or otherwise formed at desired locations of the channel 1402.

Referring to FIG. 14B, in some embodiments, the main body stent graft 1400 may include a plurality of pleated portions 1418. Each of the pleated portions 1418 may overlap with an adjacent pleated portion 1418 adluminally and/or abluminally. The pleated portions 1418 may be located at a side of the main body stent graft 1400 opposite the channel 1402, while a side of the main body stent graft 1400 including the channel 1402 may be unpleated or substantially unpleated (e.g., pleated with a slight overlap). Thus, the first and second guidewires 1410 and 1412 can be cannulated in the channel 1402, and the first and second branch portions 1406 and 1408 can be received through the channel 1402 via the first and second guidewires 1410 and 1412. Accordingly, the side of the main body stent graft 1400 opposite the first and second branch portions 1406 and 1408 may include pleated portions that overlap with an adjacent pleated portion, while the side of the main body stent graft 1400 including the first and second branch portions 1406 and 1408 do not include pleated portions or include pleated portions with a lesser overlap than those of the opposite side.

Figure 15A:
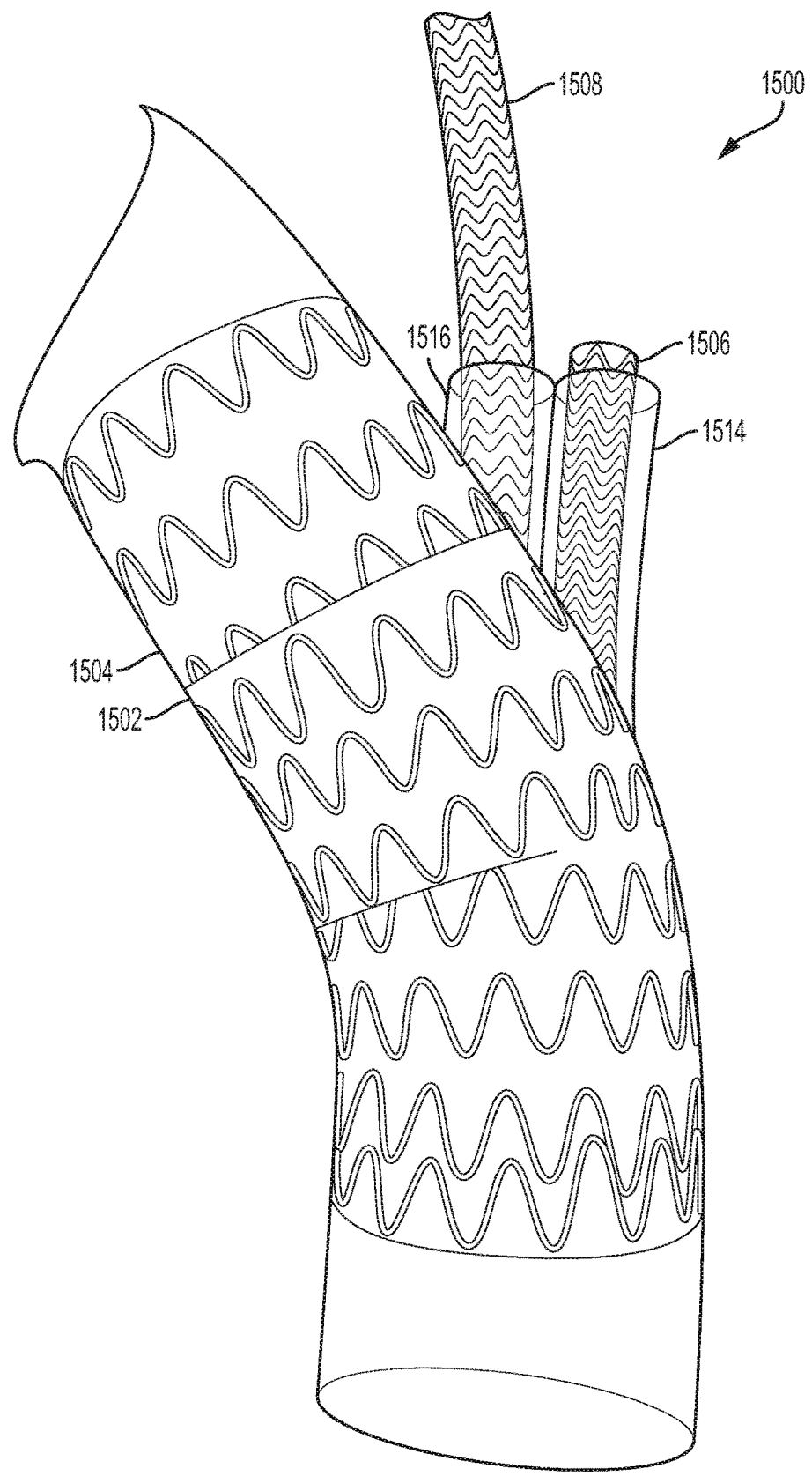
FIGS. 15A and 15B show a modular endovascular system in accordance with an embodiment.
Figure 15B:
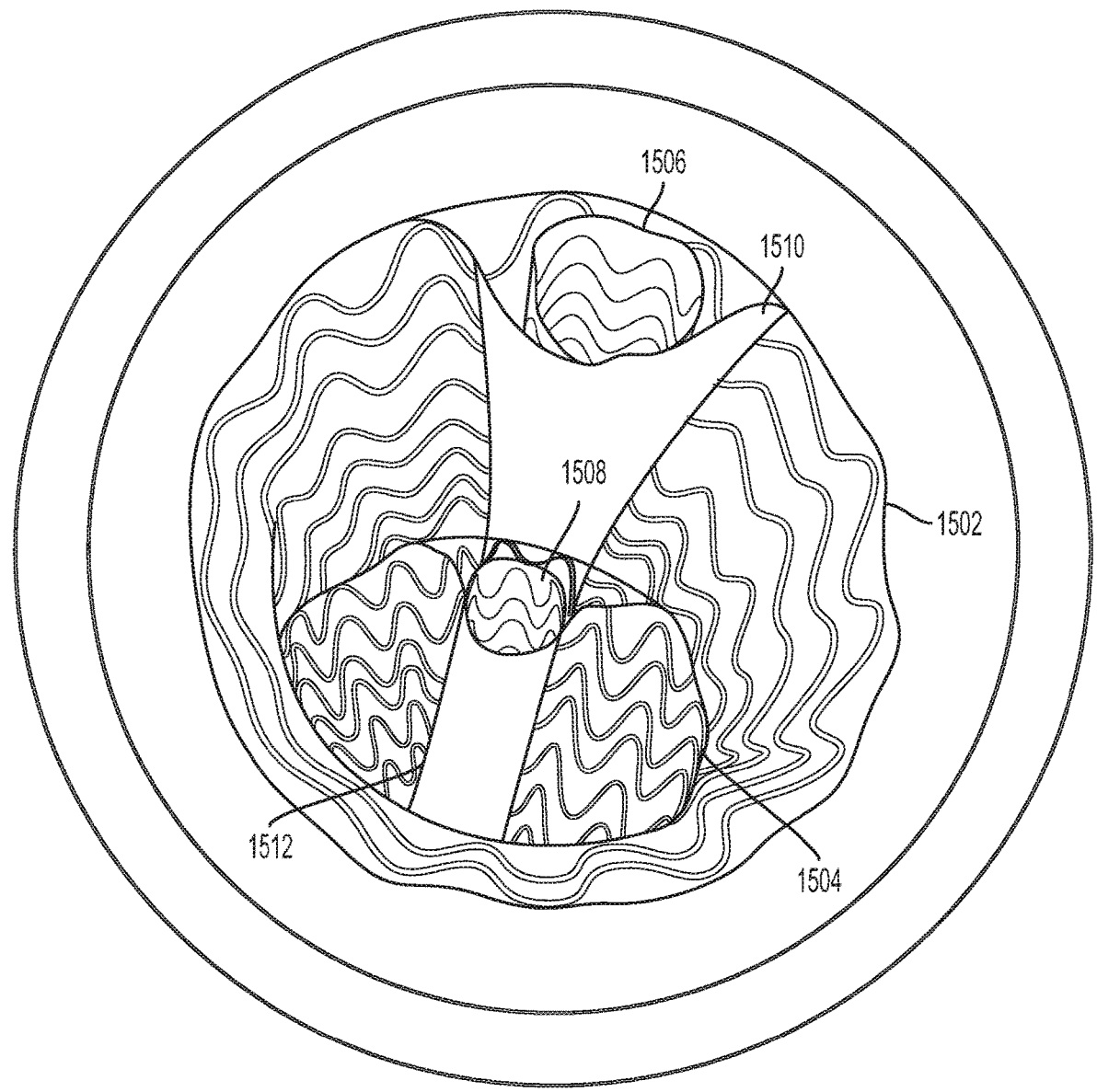

FIGS. 15A and 15B show a modular endovascular system in accordance with an embodiment. FIG. 15A is a side view of the modular endovascular system and FIG. 15B is a perspective view inside a main lumen of the modular endovascular system. The modular endovascular system in FIGS. 15A and 15B is shown as being deployed in a model of an aorta, where a first branch portion 1506 is shown as being deployed in the left common carotid artery 1514 of the aorta model, and a second branch portion 1508 is shown as being deployed in the left subclavian artery 1516 of the aorta model. Referring to FIGS. 15A and 15B, in some embodiments, the modular endovascular system 1500 includes a first main body stent graft 1502 and a second main body stent graft 1504. The first main body stent graft 1502 includes the first branch portion 1506 extending through a first channel 1510. The second main body stent graft 1504 includes the second branch portion 1508 extending through a second channel 1512. Each of the first and second channels 1510 and 1512 may be weaved, abluminal, adluminal, or any combination thereof, with respect to stent structures of the first and second main body stent graft 1502 and 1504, respectively.

In more detail, the second main body stent graft 1504 is inserted or otherwise received in a main lumen of the first main body stent graft 1502. For example, during deployment of the modular endovascular system 1500, the first main body stent graft 1502 may be positioned in the aorta as shown in FIG. 15A, via a main guidewire. Then, the second main body stent graph 1504 may be positioned to be partially inside the main lumen of the first main body stent graft 1502 as shown in FIGS. 15A and 15B, via the main guidewire. Once the first and second main body stent grafts 1502 and 1504 are positioned, the first branch portion 1506 may be guided through the first channel 1510 and positioned in the left common carotid artery 1514 via a first branch guidewire, and the second branch portion 1508 may be guided through the second channel 1512 and positioned in the left subclavian artery 1516 via a second branch guidewire. Accordingly, in various embodiments, the modular endovascular system may be successively built up into a thoracic arch as needed or desired. In the embodiment of FIGS. 15A and 15B, the flow lumens of both first and second branch portions 1506 and 1508 may be preserved despite the close proximity of the ostiums of the left common carotid artery 1514 and the left subclavian artery 1516.

Figure 16A:
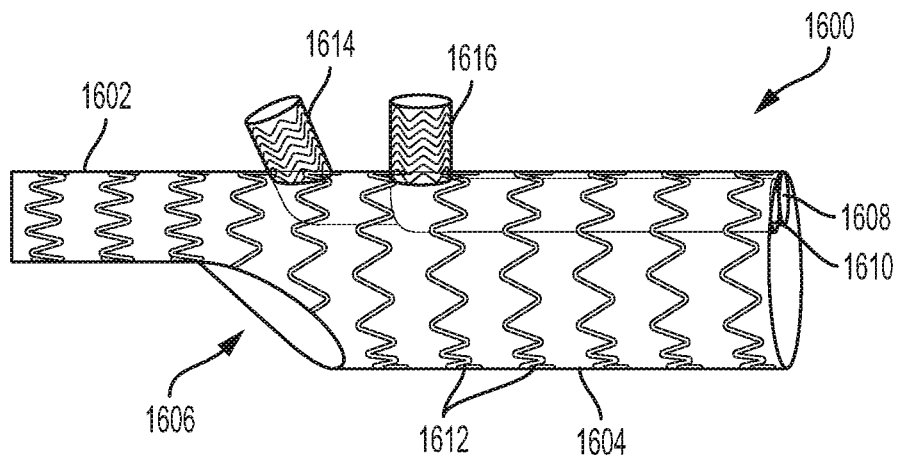
FIGS. 16A, 16B, 16C, 16D, and 16E show a modular endovascular system in accordance with an embodiment.

FIGS. 16A through 16E show a modular endovascular system in accordance with another embodiment. Referring to FIG. 16A, a modular endovascular system includes a main stent graft body 1600 having an innominate end 1602 to be deployed in an innominate artery and a main body end 1604. The main body end 1604 may include a fenestration 1606 adjacent to the innominate end 1602, such that the innominate end 1602 forms a trunk extending from the main body end 1604 at a proximal portion of the main stent graft body 1600. The main body end 1604 may further include a first channel 1608 and a second channel 1610 that may be weaved, abluminal, adluminal, or any combination thereof, with respect to a stent structure 1612 of the main body end 1604. The first channel 1608 may receive a first branch portion 1614 and the second channel 1610 may receive a second branch portion 1616.

Figure 16B:
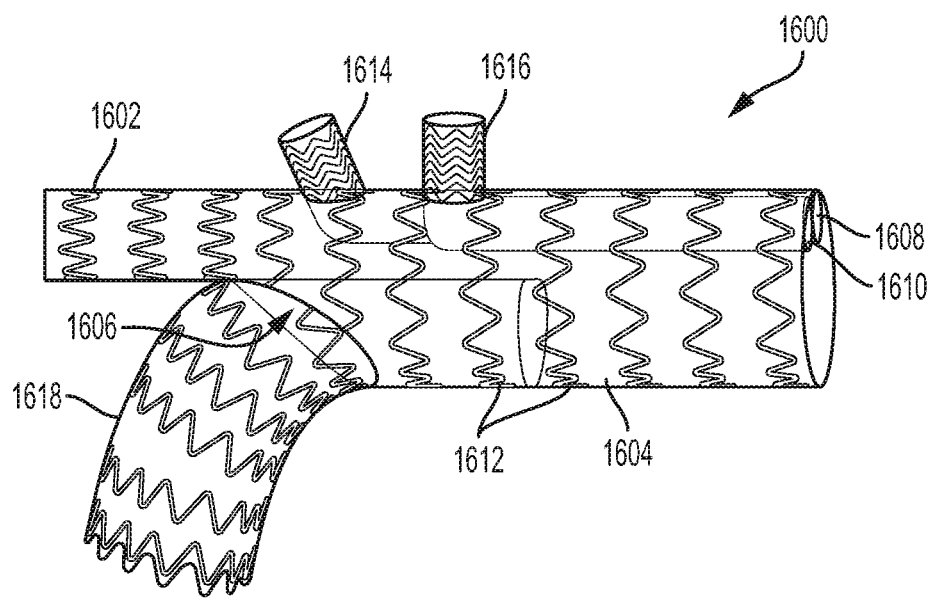
Figure 16C:
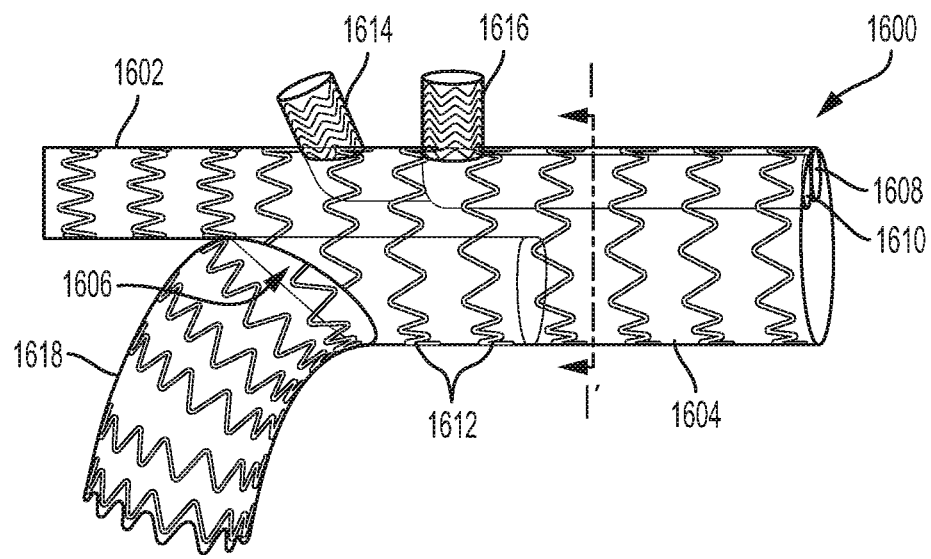
Figure 16D:
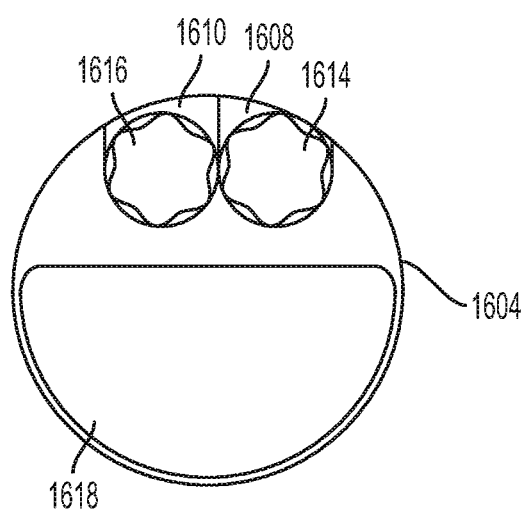

Referring to FIGS. 16B and 16C, the fenestration 1606 may receive an ascending branch portion 1618 to be deployed in an ascending aorta portion of an aorta (e.g., see FIG. 1). The ascending branch portion 1618 may extend partially through a main lumen of the main body end 1602 as shown in FIG. 16B. When the ascending branch 1618 extends partially through the main lumen of the main body end 1602, retro-grade flow path may be shortened. In another embodiment, as shown in FIG. 16C, the ascending branch portion 1618 may extend entirely through the main lumen of the main body end 1602. As shown in FIG. 16D, which is a cross-section along the line I-I' of the main body stent graft 1600 shown in FIG. 16C, the ascending branch portion 1618 is received within a lumen of the main body end 1604, such that the main body end 1604 surrounds and overlaps with a portion of the ascending branch portion 1618. While each of the first and second channels 1608 and 1610 are shown in FIG. 16C as separate channels, the present disclosure is not limited thereto. For example, in another embodiment, the first and second channels 1608 and 1610 may be the same channel having a sufficiently large width to receive both the first and second branch portions 1614 and 1616 therethrough (e.g., as described with reference to FIGS. 14A and 14B).

Figure 16E:
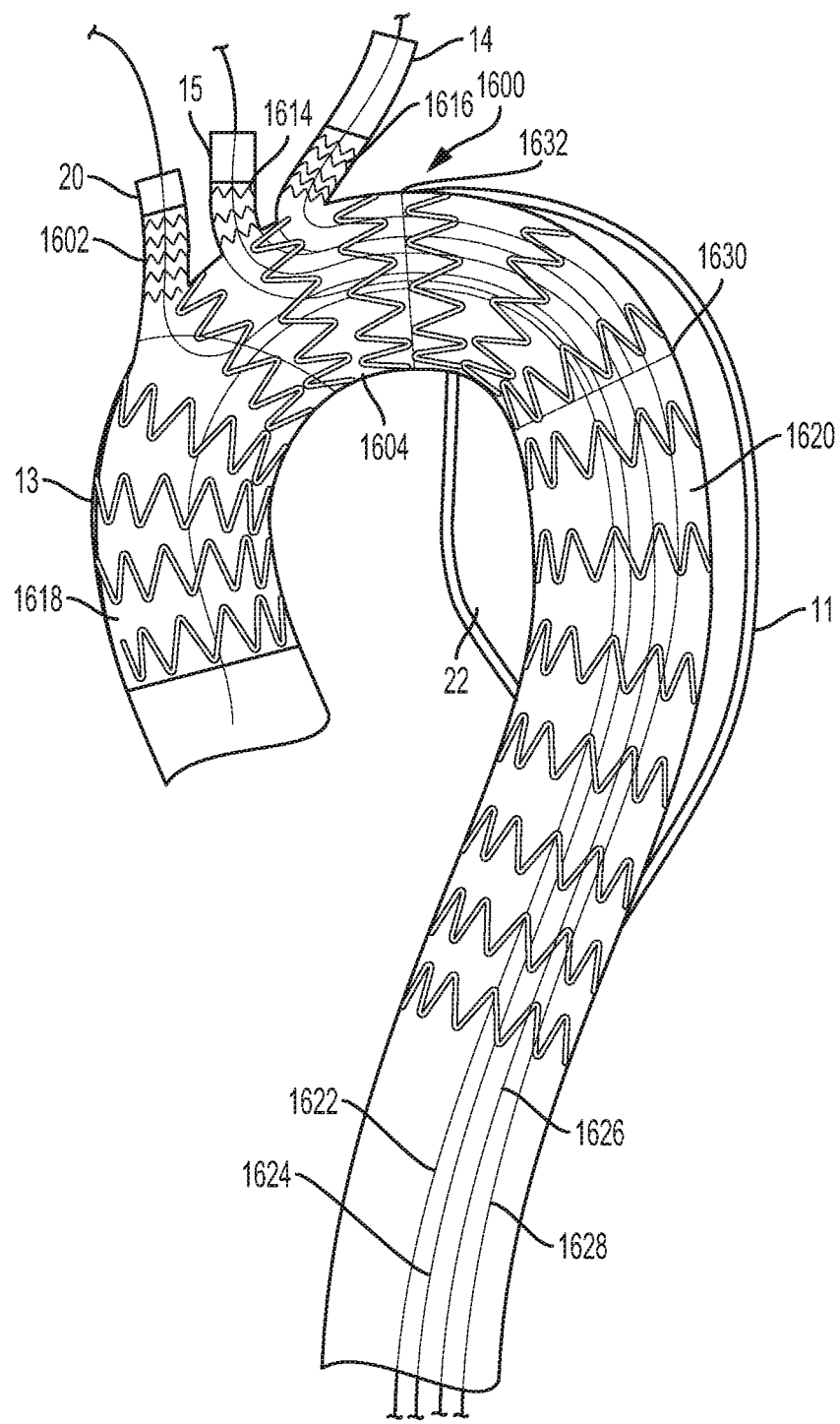

FIG. 16E shows the modular endovascular system deployed in an aorta of a human. According to various embodiments, the modular endovascular system may be successively built up into a thoracic arch, so that a partial or a full endovascular aortic repair may be performed as needed or desired. For example, referring to FIG. 16E, a descending stent graft device 1620 may first be positioned in the descending aorta portion 11. For example, the descending aorta portion 11 may have an aneurism 22, in which case the descending stent graft device 1620 may bridge the aneurism 22. The descending stent graft device 1620 may be deployed in the descending aorta portion 11 via a main body guidewire 1622. However, the present disclosure is not limited thereto, for example, the descending stent graft device 1620 may be omitted if not needed or desired.

Next, the main body stent graft 1600 may be passed through the descending stent graft device 1620 (if deployed), and may be arranged so that the innominate end 1602 is positioned in the innominate artery 20. The innominate end 1602 may be positioned in the innominate artery 20 via an innominate guidewire 1624. A distal end 1630 of the main body stent graft 1600 may remain within a proximal end 1632 of the descending stent graft device 1620, so that a portion of the descending stent graft device 1620 surrounds and overlaps with a portion of the main body stent graft 1600.

Once the main body stent graft 1600 is deployed and positioned, the first and second branch portions 1614 and 1616 may be successively deployed through the first and second channels 1608 and 1610, respectively. For example, the first branch portion 1614 may be guided through the first channel 1608 via a first branch guidewire 1626 that is cannulated in the first channel 1608. The first branch portion 1614 may be positioned in the left common carotid artery 15 via the first branch guidewire 1626. The second branch portion 1616 may be guided through the second channel 1610 via a second branch guidewire 1628 that is cannulated in the second channel 1610. The second branch portion 1616 may be positioned in the left subclavian artery 14 via the second branch guidewire 1628.

Once the first and second branch portions 1614 and 1616 are deployed and positioned, the ascending branch portion 1618 is guided through the descending stent graft device 1620 (if deployed) and the main body stent graft 1600 via the main guidewire 1622, and is positioned in the ascending aorta portion 13. A portion of the ascending branch portion 1618 may partially extend through the main lumen of the main body end 1602 (e.g., as shown in FIG. 16B), or may extend entirely through the main lumen of the main body end 1602 (e.g., as shown in FIG. 16C). Thus, the main body stent graft 1600 may surround and overlap with the portion of the ascending branch portion 1618 that extend through the main lumen of the main body end 1602. However, the present disclosure is not limited thereto, for example, the ascending branch portion 1618 may be omitted if not needed or desired.

Accordingly to various embodiments of the present disclosure, the channels effectively eliminate gutters that can be formed with sandwiched stent grafts, and since the channels can be built internally to the main body graft, the amount of effective oversizing of the endovascular system relative to the vessel wall may not be substantially changed, unlike a sandwiched graft placed externally to a main body graft.

In various embodiments, a branch portion guidewire may be pre-cannulated through the channel and wall of the main body graft, and thus, may be quickly employed with femoral access in most cases involving the left subclavian artery. Additionally, in various embodiments, placement accuracy may be improved relative to branch fenestrated systems since the branch-graft entrance remains generally parallel with the main body graft wall rather than orthogonal to main body graft wall as is the case with some fenestrated systems.

In various embodiments, an insulator sheet may be used to create a channel during the manufacturing process (e.g., lamination) of the main body stent graft. The use of the insulator sheet in various embodiments prevents layers (e.g., PTFE layers) from fusing together. In some embodiments, the insulator sheet may be wrapped or other covered with layers of PTFE, which provides support for the channel and additional separation between the branch portion and the stent structure of the main body stent graft.

In various embodiments, the branch portion receiving channel may be pre-formed on the main body stent graft, and a user (e.g., a physician or surgeon) can decide whether to use it procedurally, thereby reducing the number of different devices needed. For example, in various embodiments, a user can simply remove the pre-cannulated wire from the channel and perform a descending thoracic deployment if no branch portions are needed or desired, or the user can use the pre-cannulated wire to insert a branch portion in the channel of the main body graft to be deployed into a corresponding artery branch as needed or desired.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. Various modifications and changes that come within the meaning and range of equivalency of the claims are intended to be within the scope of the disclosure. Thus, while certain embodiments of the present disclosure have been illustrated and described, it is understood by those of ordinary skill in the art that certain modifications and changes can be made to the described embodiments without departing from the spirit and scope of the present disclosure as defined by the following claims, and their equivalents.

What is claimed is:

1. A device, comprising:
    a main body graft; and
    a channel formed at least partially on a wall of the main body graft, the channel defining a passageway for receiving a branch portion, and disposed between layers forming the main body graft; and
    a stent comprising a plurality of rings configured to support the main body graft,
    wherein the plurality of rings comprises a first ring and a second ring, and
    wherein the first ring is abluminal with respect to the channel, and the second ring is adluminal with respect to the channel.

2. The device of claim 1,
    wherein a first portion of the channel is abluminal with respect to the stent and a second portion of the channel is adluminal with respect to the stent.

3. The device of claim 1, wherein the channel is located on a first side of the main body graft, and a second side of the main body graft opposite the first side includes a plurality of pleated portions.

4. The device of claim 3, wherein the first side is substantially not pleated.

5. A system, comprising:
    a branch portion comprising a stent graft;
    a main body graft having a main lumen;
    a stent configured to support the main body graft comprising a first ring and a second ring; and
    a channel within the main lumen defining a passageway for receiving the branch portion,
    wherein the first ring is abluminal with respect to the channel, and the second ring is adluminal with respect to the channel.

6. The system of claim 5,
    wherein a first portion of the channel is abluminal with respect to the stent and a second portion of the channel is adluminal with respect to the stent.

7. The system of claim 5, wherein the channel is partially disposed between layers forming the main body graft and partially outside the graft layers within the main lumen.

8. The system of claim 5, wherein the channel is located on a first side of the main body graft, and a second side of the main body graft opposite the first side includes a plurality of pleated portions.

9. The system of claim 5, wherein the first side is substantially not pleated.

10. A method comprising:
    forming a main body stent graft comprising a stent having a plurality of rings configured to support said main body graft; and
    forming a channel at least partially on a wall of the main body graft, the channel defining a passageway for receiving a branch portion,
    wherein the channel is disposed between layers forming the main body graft,
    wherein the plurality of rings comprises a first ring and a second ring, and
    wherein the first ring is abluminal with respect to the channel, and the second ring is adluminal with respect to the channel.

11. The method of claim 10, wherein the forming of the main body stent graft comprises: forming one or more inner graft layers; and
    disposing the stent structure on the one or more inner graft layers.

12. The method of claim 11, wherein the forming of the channel comprises:
    disposing an insulator sheet on the stent structure;
    forming one or more outer graft layers on the insulator sheet and the stent structure; heating the main body stent graft; and
    removing the insulator sheet.

13. The method of claim 12, wherein the insulator sheet comprises poly-oxydiphenylene pyromellitimide.

14. The method of claim 12, wherein the insulator sheet is wrapped with a graft material, and the graft material fuses with at least one of the inner graft layers or outer graft layers when the main body stent graft is heated.

15. The method of claim 14, further comprising:
    disposing a first separator sheet between the insulator sheet and the stent structure; and
    disposing a second separator sheet between the insulator sheet and the stent structure, the second separator sheet being spaced apart from the first separator sheet to define a space therebetween, wherein the graft material fuses with at least one of the inner graft layers or outer graft layers in the space when the main body stent graft is heated.

* * * * *